United States Patent
Jarvius et al.

(10) Patent No.: US 12,247,192 B2
(45) Date of Patent: Mar. 11, 2025

(54) MEDICAL SAMPLE TRANSPORTATION CONTAINER

(71) Applicant: Q-linea AB, Uppsala (SE)

(72) Inventors: Jonas Jarvius, Uppsala (SE); Anders Lind, Tarnsjo (SE); Henrik Soderstrom, Knivsta (SE); Jan Grawe, Uppsala (SE); Ian Fitzpatrick, Elwood (AU); Jurg Bartholdi, San Diego, CA (US)

(73) Assignee: Q-Linea AB, Uppsala (SE)

( * ) Notice: Subject to any disclaimer, the term of this patent is extended or adjusted under 35 U.S.C. 154(b) by 164 days.

(21) Appl. No.: 17/214,192

(22) Filed: Mar. 26, 2021

(65) Prior Publication Data

US 2021/0246410 A1    Aug. 12, 2021

Related U.S. Application Data

(62) Division of application No. 15/569,036, filed as application No. PCT/EP2016/058952 on Apr. 21, 2016, now Pat. No. 10,995,311.

(30) Foreign Application Priority Data

Apr. 24, 2015    (GB) .................... 1507026

(51) Int. Cl.
*C12M 3/00*    (2006.01)
*A01N 1/00*    (2006.01)
(Continued)

(52) U.S. Cl.
CPC ............ *C12M 41/14* (2013.01); *A01N 1/0252* (2013.01); *A01N 1/0273* (2013.01); *C12M 27/16* (2013.01); *C12M 41/24* (2013.01); *C12Q 1/04* (2013.01)

(58) Field of Classification Search
CPC ...... C12M 41/14; C12M 27/16; A01N 1/0273
See application file for complete search history.

(56) References Cited

U.S. PATENT DOCUMENTS

| 3,159,384 A | 12/1964 | Davis |
| 3,764,780 A * | 10/1973 | Ellis ..................... B01L 7/00 165/47 |

(Continued)

FOREIGN PATENT DOCUMENTS

| CN | 1248295 A | 3/2000 |
| CN | 2436459 Y | 6/2001 |

(Continued)

OTHER PUBLICATIONS

AliFax SRL, "Alfred 60$^{AST}$—First Automated System for Bacterial Culture and Susceptibility Testing", Alifax SRL, Italy (2015) 2 pages.

(Continued)

*Primary Examiner* — Nathan A Bowers
(74) *Attorney, Agent, or Firm* — Lippes Mathias LLP

(57) ABSTRACT

A portable apparatus and method for transport and incubation of a medical sample in a blood culture flask includes a sealable container having a thermally insulated compartment for receiving the blood culture flask and a heater for heating the medical sample to a temperature suitable for pre-culturing of the sample. An agitator is provided for agitating the sample in the blood culture flask.

20 Claims, 6 Drawing Sheets

(51) Int. Cl.
*A01N 1/02* (2006.01)
*C12M 1/00* (2006.01)
*C12M 1/02* (2006.01)
*C12M 3/06* (2006.01)
*C12Q 1/04* (2006.01)

(56) References Cited

U.S. PATENT DOCUMENTS

| | | | |
|---|---|---|---|
| 3,975,001 A | 8/1976 | Moore et al. | |
| 4,004,883 A | 1/1977 | Meyer et al. | |
| 4,629,686 A | 12/1986 | Gruenberg | |
| 4,666,850 A | 5/1987 | Mehl et al. | |
| 4,812,408 A * | 3/1989 | Hammann | C12M 23/34 |
| | | | 215/276 |
| 4,886,071 A | 12/1989 | Mehl et al. | |
| 5,052,812 A * | 10/1991 | Tannenbaum | B01F 31/22 |
| | | | 366/209 |
| 5,143,854 A | 9/1992 | Pirrung et al. | |
| 5,183,994 A | 2/1993 | Bowles, Sr. et al. | |
| 5,217,876 A | 6/1993 | Turner et al. | |
| 5,238,302 A * | 8/1993 | Rohan | B01F 31/201 |
| | | | 366/208 |
| 5,316,146 A | 5/1994 | Graff | |
| 5,405,783 A | 4/1995 | Pirrung et al. | |
| 5,445,934 A | 8/1995 | Fodor et al. | |
| 5,510,267 A | 4/1996 | Marshall | |
| 5,577,837 A | 11/1996 | Martin et al. | |
| 5,744,305 A | 4/1998 | Fodor et al. | |
| 5,770,394 A | 6/1998 | Berndt | |
| 5,789,173 A | 8/1998 | Peck et al. | |
| 5,817,508 A | 10/1998 | Berndt | |
| 5,882,918 A | 3/1999 | Goffe | |
| 5,945,334 A | 8/1999 | Besemer et al. | |
| 6,028,293 A | 2/2000 | Nagle et al. | |
| 6,059,446 A | 5/2000 | Dschida | |
| 6,083,763 A | 7/2000 | Balch | |
| 6,093,551 A | 7/2000 | Raithel et al. | |
| 6,096,532 A | 8/2000 | Armstrong et al. | |
| 6,143,495 A | 11/2000 | Lizardi et al. | |
| 6,183,960 B1 | 2/2001 | Lizardi | |
| 6,225,625 B1 | 5/2001 | Pirrung et al. | |
| 6,261,776 B1 | 7/2001 | Pirrung et al. | |
| 6,291,183 B1 | 9/2001 | Pirrung et al. | |
| 6,310,189 B1 | 10/2001 | Fodor et al. | |
| 6,329,143 B1 | 12/2001 | Stryer et al. | |
| 6,354,104 B1 * | 3/2002 | Feagin | A61B 10/0096 |
| | | | 70/68 |
| 6,403,957 B1 | 6/2002 | Fodor et al. | |
| 6,406,844 B1 | 6/2002 | Pirrung et al. | |
| 6,630,308 B2 | 10/2003 | Stryer et al. | |
| 6,646,243 B2 | 11/2003 | Pirrung et al. | |
| 6,660,234 B2 | 12/2003 | Stryer et al. | |
| 6,747,143 B2 | 6/2004 | Stryer et al. | |
| 6,803,208 B2 | 10/2004 | Seaver et al. | |
| 7,008,788 B2 | 3/2006 | Schremp et al. | |
| 7,087,732 B2 | 8/2006 | Fodor et al. | |
| 7,223,363 B2 | 5/2007 | McNeely et al. | |
| 7,235,400 B2 | 6/2007 | Adey | |
| 7,334,516 B2 * | 2/2008 | Ho | C12H 1/16 |
| | | | 366/144 |
| 7,341,841 B2 | 3/2008 | Metzger et al. | |
| 7,387,883 B2 | 6/2008 | Walsh et al. | |
| 7,547,526 B2 | 6/2009 | Ladisch et al. | |
| 7,687,239 B2 | 3/2010 | Goldberg et al. | |
| 7,790,388 B2 | 9/2010 | Landegren et al. | |
| 7,893,251 B2 | 2/2011 | Lorenz | |
| 8,071,319 B2 | 12/2011 | Metzger et al. | |
| 8,074,465 B2 | 12/2011 | Heroux et al. | |
| 8,288,522 B2 | 10/2012 | Luo et al. | |
| 8,460,887 B2 | 6/2013 | Goldberg et al. | |
| 8,481,265 B2 | 7/2013 | Peytavi et al. | |
| 8,603,769 B2 | 12/2013 | Feng et al. | |
| 8,609,024 B2 | 12/2013 | Ronsick et al. | |
| 8,652,800 B2 | 2/2014 | Walsh et al. | |
| 8,709,344 B2 | 4/2014 | Bishop et al. | |
| 8,709,748 B2 | 4/2014 | Walsh et al. | |
| 8,780,181 B2 | 7/2014 | Olesen et al. | |
| 8,841,118 B2 | 9/2014 | Robinson et al. | |
| 8,846,897 B2 | 9/2014 | Euting et al. | |
| 8,895,255 B1 | 11/2014 | Goldberg et al. | |
| 8,911,987 B2 | 12/2014 | Robinson et al. | |
| 8,937,174 B2 | 1/2015 | Rothmann et al. | |
| 10,655,188 B2 | 5/2020 | Jarvius | |
| 2002/0055101 A1 | 5/2002 | Bergeron et al. | |
| 2003/0098271 A1 | 5/2003 | Somack et al. | |
| 2003/0235853 A1 | 12/2003 | Stryer et al. | |
| 2005/0037408 A1 | 2/2005 | Christensen et al. | |
| 2005/0042144 A1 * | 2/2005 | Hubbard | B01L 7/04 |
| | | | 422/400 |
| 2005/0064469 A1 | 3/2005 | Schulz et al. | |
| 2005/0095665 A1 | 5/2005 | Williams et al. | |
| 2005/0148027 A1 | 7/2005 | Pirrung et al. | |
| 2005/0202487 A1 | 9/2005 | Klepp et al. | |
| 2005/0214828 A1 | 9/2005 | Pirrung et al. | |
| 2006/0020579 A1 | 1/2006 | Freedman et al. | |
| 2006/0029972 A1 | 2/2006 | Lorenz | |
| 2006/0094034 A1 | 5/2006 | Brousseau et al. | |
| 2006/0223098 A1 | 10/2006 | Lane et al. | |
| 2008/0029247 A1 | 2/2008 | Nozaki et al. | |
| 2008/0139865 A1 | 6/2008 | Galliher et al. | |
| 2008/0145919 A1 | 6/2008 | Franklin et al. | |
| 2008/0160528 A1 | 7/2008 | Lorenz | |
| 2009/0209031 A1 | 8/2009 | Stopek | |
| 2010/0124763 A1 | 5/2010 | Walsh et al. | |
| 2010/0184210 A1 | 7/2010 | Rossmanith et al. | |
| 2010/0255474 A1 | 10/2010 | Russwurm et al. | |
| 2010/0288060 A1 | 11/2010 | Ronsick et al. | |
| 2010/0291615 A1 | 11/2010 | Ronsick et al. | |
| 2010/0291619 A1 | 11/2010 | Robinson et al. | |
| 2010/0291669 A1 | 11/2010 | Robinson et al. | |
| 2010/0297645 A1 | 11/2010 | Pierik et al. | |
| 2010/0311108 A1 | 12/2010 | Bishop et al. | |
| 2011/0092691 A1 | 4/2011 | Euting et al. | |
| 2011/0124028 A1 | 5/2011 | Robinson et al. | |
| 2011/0124029 A1 | 5/2011 | Remes et al. | |
| 2011/0124030 A1 | 5/2011 | Philipak et al. | |
| 2011/0124038 A1 | 5/2011 | Bishop et al. | |
| 2011/0124096 A1 | 5/2011 | Philipak et al. | |
| 2011/0125314 A1 | 5/2011 | Robinson et al. | |
| 2012/0009577 A1 | 1/2012 | Luo et al. | |
| 2012/0077206 A1 | 3/2012 | Metzger et al. | |
| 2012/0115183 A1 | 5/2012 | Clay | |
| 2012/0149599 A1 | 6/2012 | Williams et al. | |
| 2012/0231446 A1 | 9/2012 | Heckel et al. | |
| 2013/0011905 A1 | 1/2013 | Rapoport et al. | |
| 2013/0045532 A1 | 2/2013 | Hyman et al. | |
| 2013/0065223 A1 | 3/2013 | Klein et al. | |
| 2013/0071615 A1 | 3/2013 | Murata et al. | |
| 2013/0171615 A1 | 7/2013 | Van Meerbergen et al. | |
| 2013/0183717 A1 | 7/2013 | Marble et al. | |
| 2013/0184446 A1 | 7/2013 | Marble et al. | |
| 2013/0217063 A1 | 8/2013 | Metzger et al. | |
| 2013/0224729 A1 | 8/2013 | Church et al. | |
| 2013/0226032 A1 | 8/2013 | Mitsuhashi et al. | |
| 2013/0252271 A1 | 9/2013 | Ullery | |
| 2013/0261196 A1 | 10/2013 | Diamond et al. | |
| 2014/0072998 A1 | 3/2014 | Ronsick et al. | |
| 2014/0087361 A1 | 3/2014 | Dobbelaer et al. | |
| 2014/0278136 A1 | 9/2014 | Shamsheyeva et al. | |
| 2014/0287408 A1 | 9/2014 | Su et al. | |
| 2014/0323340 A1 | 10/2014 | Goldberg et al. | |
| 2015/0031074 A1 | 1/2015 | Robinson et al. | |
| 2015/0132793 A1 | 5/2015 | Penterman et al. | |
| 2015/0225762 A1 | 8/2015 | Metzger et al. | |
| 2015/0344973 A1 | 12/2015 | Rolfe et al. | |
| 2016/0010138 A1 | 1/2016 | Shamsheyeva | |
| 2016/0053219 A1 | 2/2016 | Walker et al. | |
| 2016/0281130 A1 | 9/2016 | Dahl et al. | |
| 2017/0320054 A1 * | 11/2017 | Crum | B01L 9/06 |
| 2020/0318164 A1 | 10/2020 | Jarvius | |

(56) References Cited

U.S. PATENT DOCUMENTS

FOREIGN PATENT DOCUMENTS

| | | |
|---|---|---|
| CN | 101130808 A | 2/2008 |
| CN | 101680041 A | 3/2010 |
| CN | 101745440 A | 6/2010 |
| CN | 101845390 A | 9/2010 |
| CN | 102272601 A | 12/2011 |
| CN | 204255722 U | 4/2015 |
| EP | 0122581 A2 | 10/1984 |
| EP | 0143329 A2 | 6/1985 |
| EP | 0745140 A1 | 12/1996 |
| EP | 0745849 A2 | 12/1996 |
| EP | 0834553 A2 | 4/1998 |
| EP | 0853658 A1 | 7/1998 |
| EP | 0951565 A1 | 10/1999 |
| EP | 0964704 A1 | 12/1999 |
| EP | 1467815 A1 | 10/2004 |
| EP | 1527172 A1 | 5/2005 |
| EP | 1574583 A1 | 9/2005 |
| EP | 1648286 A2 | 4/2006 |
| EP | 1861495 A1 | 12/2007 |
| EP | 1945821 A1 | 7/2008 |
| EP | 2049677 A1 | 4/2009 |
| EP | 2056114 A1 | 5/2009 |
| EP | 2185681 A1 | 5/2010 |
| EP | 2208075 A2 | 7/2010 |
| EP | 2333105 A1 | 6/2011 |
| EP | 2430445 A2 | 3/2012 |
| EP | 2430456 A2 | 3/2012 |
| EP | 2430457 A2 | 3/2012 |
| EP | 2430459 A2 | 3/2012 |
| EP | 2430460 A2 | 3/2012 |
| EP | 2430461 A2 | 3/2012 |
| EP | 2501811 A1 | 9/2012 |
| EP | 2510123 A1 | 10/2012 |
| EP | 2571976 A1 | 3/2013 |
| EP | 2684947 A1 | 1/2014 |
| EP | 2718713 A1 | 4/2014 |
| EP | 2734280 A1 | 5/2014 |
| EP | 2828398 A1 | 1/2015 |
| EP | 2870233 A1 | 5/2015 |
| EP | 2872523 A2 | 5/2015 |
| EP | 2288701 B1 | 6/2015 |
| EP | 2893344 A1 | 7/2015 |
| EP | 2942394 A1 | 11/2015 |
| EP | 2971055 A1 | 1/2016 |
| EP | 3077541 A2 | 10/2016 |
| GB | 2055530 A | 3/1981 |
| GB | 2520765 A | 6/2015 |
| JP | H08285839 A | 11/1996 |
| JP | 2001-103981 A | 4/2001 |
| JP | 2001-169778 A | 6/2001 |
| JP | 2002-502583 A | 1/2002 |
| JP | 2002-532103 A | 10/2002 |
| JP | 2005-502354 A | 3/2004 |
| JP | 2006-525809 A | 11/2005 |
| JP | 2006-508696 A | 3/2006 |
| JP | 2006-516193 A | 6/2006 |
| JP | 2010-537650 A | 12/2010 |
| JP | 2013-520206 A | 6/2013 |
| JP | 2013-255445 A | 12/2013 |
| JP | 2014-514930 A | 6/2014 |
| RU | 2 228 735 C2 | 1/2004 |
| WO | WO 84/02721 A1 | 7/1984 |
| WO | WO 86/00139 A1 | 1/1986 |
| WO | WO 88/06189 A1 | 8/1988 |
| WO | WO 93/16384 A1 | 8/1993 |
| WO | WO 97/12029 A1 | 4/1997 |
| WO | WO 00/71675 A1 | 11/2000 |
| WO | WO 00/72970 A1 | 12/2000 |
| WO | WO 01/12199 A2 | 2/2001 |
| WO | WO 2003/022999 A2 | 3/2003 |
| WO | WO 03/059516 A1 | 7/2003 |
| WO | WO 03/097831 A1 | 11/2003 |
| WO | WO 2005017202 | 2/2005 |
| WO | WO 2005/027714 A2 | 3/2005 |
| WO | WO 2005/068647 A2 | 7/2005 |
| WO | WO 2005/093045 A2 | 10/2005 |
| WO | WO 2006/020579 A2 | 2/2006 |
| WO | WO 2006/092278 A1 | 9/2006 |
| WO | WO 2007/035504 A1 | 3/2007 |
| WO | WO 2007/033051 A2 | 9/2007 |
| WO | WO 2008/017097 A1 | 2/2008 |
| WO | WO 2009/015484 A1 | 2/2009 |
| WO | WO 2009/057014 A2 | 5/2009 |
| WO | WO 2009/098104 A1 | 8/2009 |
| WO | WO 2009/153299 A1 | 12/2009 |
| WO | WO 2010/048511 A1 | 4/2010 |
| WO | WO 2010/062356 A1 | 6/2010 |
| WO | WO 2010/132741 A2 | 11/2010 |
| WO | WO 2010/132746 A2 | 11/2010 |
| WO | WO 2010/132749 A2 | 11/2010 |
| WO | WO 2010/132780 A2 | 11/2010 |
| WO | WO 2010/132805 A2 | 11/2010 |
| WO | WO 2010/132823 A2 | 11/2010 |
| WO | WO 2010/132829 A2 | 11/2010 |
| WO | WO 2011/019874 A1 | 2/2011 |
| WO | WO 2011/061274 A1 | 5/2011 |
| WO | WO 2011/070507 A1 | 6/2011 |
| WO | WO 2011/144304 A1 | 11/2011 |
| WO | WO 2012/162133 A1 | 11/2012 |
| WO | WO 2012/168003 A1 | 12/2012 |
| WO | WO 2013/016211 A1 | 1/2013 |
| WO | WO 2013/142347 A1 | 9/2013 |
| WO | WO 2013/163210 A1 | 10/2013 |
| WO | WO 2014/009151 A1 | 1/2014 |
| WO | WO 2014/040088 A1 | 3/2014 |
| WO | WO 2014/076209 A1 | 5/2014 |
| WO | WO 2014/145899 A1 | 9/2014 |
| WO | WO 2014/160352 A1 | 10/2014 |
| WO | WO 2015/079042 A1 | 6/2015 |
| WO | WO 2015/083002 A2 | 6/2015 |
| WO | WO 2015/169933 A2 | 11/2015 |
| WO | WO 2015/189390 A1 | 12/2015 |
| WO | WO 2016/033077 A1 | 3/2016 |

OTHER PUBLICATIONS

Anderson, Rolfe C. et al., "A Miniature Integrated Device for Automated Multistep Genetic Assays", Nucleic Acids Research, vol. 28, No. 12 (2000) pp. i-vi.

Antson, D.-O. et al., "PCR-Generated Padlock Probes Detect Single Nucleotide Variation in Genomic DNA", Nucleic Acids Research, vol. 28, No. 12 (2000) pp. i-vi.

Baker, Zelma et al., "The Bactericidal Action of Synthetic Detergents", Walter G. Zoller Memorial Dental Clinic, the Department of Bacteriology and Parasitology, and the Department of Medicine, The University of Chicago (1941) pp. 611-620.

Baner, Johan et al., "Signal Amplification of Padlock Probes by Rolling Circle Replication", Nucleic Acids Reasearch, vol. 26, No. 22 (1998) pp. 5073-5078.

Baner, Johan et al., "Parallel Gene Analysis With Allele-Specific Padlock Probes and Tag Microarrays", Nucleic Acids Research, vol. 31, No. 17 (2003) pp. 1-7.

Baner, Johan et al., "Microarray-Based Molecular Detection of Foot-And-Mouth Disease, Vesicular Stomatitis and Swine Vesicular Disease Viruses, Using Padlock Probes", Journal of Virological Methods, 143 (2007) pp. 200-206.

Barisic, Ivan et al., "Multiplex Detection ff Antibiotic Resistance Genes Using Padlock Probes", Diagnostic Microbiology and Infectious Disease, 77 (2013) pp. 118-125.

BD Diagnostics, "BD Phoenix, Automated Microbiology System" (2008) 13 pages.

BD Diagnostics, "BD Phoenix ID/AST Manual Panel Inoculation" (2012) 1 page.

BD Phoenix, Laboratory Procedure, pp. 1-30, at least as early as Jun. 13, 2014.

BioMerieux SA, "Vitek 2 Instrument User Manual" (2008) 218 pages.

(56) References Cited

OTHER PUBLICATIONS

Birnboim, H. C. et al., "A Rapid Alkaline Extraction Procedure for Screening Recombinant Plasmid DNA", Nucleic Acids Research, vol. 7, No. 6 (1979) pp. 1513-1524.
Broeren, M. A. C. et al., "Antimicrobial Susceptibility Testing in 90 Min by Bacteria Cell Count Monitoring", Clinical Microbiology and Infection, vol. 19, No. 3 (2013) pp. 286-291.
Brooks, Mark et al., "Policy for the Transport of Pathology Samples", Pathology—Transport of Pathology Samples GP/MP6, Version 3.4, Aug. 2014, pp. 1-11.
Brown, Deborah A. et al., "Sorting of GPI-Anchored Proteins to Glycolipid-Enriched Membrane Subdomains During Transport to the Apical Cell Surface", Cell, vol. 68 (1992) pp. 533-544.
Chandler, Darrell P. et al., "Integrated Amplification Microarrays for Infectious Disease Diagnostics", Microarrays, 1 (2012) pp. 107-124.
Dahl, Fredrik et al., "Circle-To-Circle Amplification for Precise and Sensitive DNA Analysis", PNAS, vol. 101, No. 13 (2004) pp. 4548-4553.
De Jong, Ymke, "A Fast Antibiotic Susceptibility Test by Direct Staining", Uppsala Universitet, Thesis Report (2014) pp. 1-23.
Fire, Andrew et al., "Rolling Replication of Short DNA Circles", Proc. Natl. Acad. Sci. USA, vol. 92 (1995) pp. 4641-4645.
Fredborg, Marlene et al., "Real-Time Optical Antimicrobial Susceptibility Testing", Journal of Clinical Microbiology, vol. 51, No. 7 (2013) pp. 2047-2053.
GE Healthcare Lifesciences Handbook, "Nucleic Acid Sample Preparation for Downstream Analyses" (2013) 168 pages.
Giacomazzi, C. G., et al, "Rapid diagnosis of tuberculosis and multidrug resistance with the microscopic observation drug susceptibility assay in Ecuador." Int. J. Tuberc. Lung Dis., vol. 14, No. 6, pp. 786-788 (2010).
Göransson et al., "Rapid Identification of Bio-Molecules Applied for Detection of Biosecurity Agents Using Rolling Circle Amplification", Plos One, vol. 7, No. 2, (2012), pp. 1-9.
Gyarmati, Peter et al., "Simultaneous Genotyping of All Hemagglutinin and Neuraminidase Subtypes of Avian Influenza Viruses by Use of Padlock Probes", Journal of Clinical Microbiology, vol. 46, No. 5 (2008) pp. 1747-1751.
Handschur, M. Karlic et al., "Preanalytic Removal of Human DNA Eliminates False Signals in General 16S rDNA PCR Monitoring of Bacterial Pathogens in Blood", Comp. Immun. Microbiol. Infect. Dis., vol. 32 (2009) pp. 207-219.
Hardenbol, Paul et al., "Multiplexed Genotyping With Sequence-Tagged Molecular Inversion Probes", Nature Biotechnology, vol. 21, No. 6 (2003) pp. 673-678.
Harrison, Susan T. L., "Bacterial Cell Disruption: A Key Unit Operation in the Recovery of Intracellular Products", Biotech. Adv., vol. 9 (1991) pp. 217-240.
Hu, Wenqi et al., "Application of Nucleic Acid Hybridization Technology in Detection of Environmental Microorganism", Microbiology China, vol. No. 22, Issue No. 6, Dec. 31, 1995 (w/English Translation) 15 pages.
Ishii, Reina et al., "Counting Single DNA Molecule by On-Bead Rolling Circle Amplification for Quantitative Analyses", 15th International Conference on Miniaturized Systems for Chemistry and Life Sciences (2011) pp. 70-72.
Ichiyama, Satoshi et al. "*Mycobacterium* Growth Indicator Tube Testing in Conjunction with the AccuProbe or the AMPLICOR-PCR Assay for Detecting and Identifying Mycobacteria from Sputum Samples", J. Clin. Microbial., vol. 35, No. 8, Aug. 1997, pp. 2022-2025.
Ichiyama, Satoshi, "A Protocol for the Rapid Diagnosis of Pulmonary Tuberculosis", Medical Technology, 2000, vol. 28, No. 12, pp. 1324-1329 (with English Translation).
Jarvius, Jonas et al., "Digital Quantification Using Amplified Single-Molecule Detection", Nature Methods, vol. 3, No. 9 (2006) pp. 725-727 (with Supplementary note—16 pages).

Jorgensen et al., "Antimicrobial Susceptibility Testing: A Review of General Principles and Contemporary Practices", Clinical Infectious Diseases, vol. 49, No. 11, (2009), pp. 1749-1755.
Kagan, Robert L. et al., "Rapid Automated Diagnosis of Bacteremia by Impedance Detection", Journal of Clinical Microbiology, vol. 5, No. 1 (1977) pp. 51-57.
Ke, Rongqin et al., "Colorimetric Nucleic Acid Testing Assay for RNA Virus Detection Based on Circle-To-Circle Amplification of Padlock Probes", Journal of Clinical Microbiology, vol. 49, No. 12 (2011) pp. 4279-4285.
Kesberg, Anna Isabella et al., "Improved Protocol for Recovery of Bacterial DNA From Water Filters: Sonication and Backflushing of Commercial Syringe Filters", Journal of Microbiological Methods, 93, 2 (2013) pp. 1-7.
Koltai, Hinanit et al., "Survey and Summary—Specificity of DNA Microarray Hybridization: Characterization, Effectors and Approaches for Data Correction", Nucleic Acids Research, vol. 36, No. 7 (2008) pp. 2395-2405.
Kumar MD, Anand et al., "Duration of Hypotension Before Initiation of Effective Antimicrobial Therapy Is the Critical Determinant of Survival in Human Septic Shock", Critical Care Medicine, vol. 34, No. 6 (2006) pp. 1589-1596.
Lahanas, Sophie et al., "Evaluation of the Alfred 60/AST as a Screening Test for Urinary Tract Infections", Journal of Clinical Microbiology (2013) pp. 1-13.
Landegren, Ulf et al., "A Ligase-Mediated Gene Detection Technique", Science, vol. 241 (1988) pp. 1077-1080.
Larsson, Chatarina et al., "In Situ Genotyping Individual DNA Molecules by Target-Primed Rolling-Circle Amplification of Padlock Probes", Nature Methods, vol. 1, No. 3 (2004) pp. 227-232.
Liesenfeld, O. et al., "Molecular Diagnosis of Sepsis: New Aspects and Recent Developments", European Journal of Microbiology and Immunology, 4, 1 (2014) pp. 1-25.
Liu, Quanjun et al., "Microarray-In-A-Tube for Detection of Multiple Viruses", Clinical Chemistry, 53:2 (2007) pp. 188-194.
Lizardi, Paul M. et al., "Mutation Detection and Single-Molecule Counting Using Isothermal Rolling-Circle Amplification", Nature Genetics, vol. 19 (1998) pp. 225-232.
Loonen, Anne J. M. et al. "Comparison of Pathogen DNA Isolation Methods From Large Volumes of Whole Blood to Improve Molecular Diagnosis of Bloodstream Infections", PLOS One, vol. 8, Issue 8 (2013) pp. 1-7.
Lorenz, Michael, "SelectNA Plus—Walk-Away Automated Extraction of Microbial DNA From Clinical Samples", Molzym GmbH & Co. KG, Molzym's Tapas Symposium Direct Molecular Testing (2014) pp. 1-6.
Metzger, S. et al., "Direct Identification of Methicillin Resistant *Staphylococcus aureus* (MRSA) Using Small Numbers of Immobilized Cells and Response to Oxacillin (OXA) by Automated Growth Analysis", ASM, Accelr8 Technology Corporation (2007), 1 page.
Metzger, S. et al., "Rapid Identification of Resistance Phenotypes in Gram-Negative Bacilli Using Automated Digital Microscopy", ASM, Accelr8 Technology Corporation (2009), 1 page.
Metzger, S. et al., "Same-Day ID and Resistance Phenotyping Directly From Respiratory Specimens by Automated Microscopy", ASM, Accelr8 Technology Corporation (2011), 1 page.
Metzger, S. et al., "Rapid Simultaneous Identification and Quantitation of *Staphylococcus aureus* and *Pseudomonas aeruginosa* Directly From Bronchoalveolar Lavage Specimens Using Automated Microscopy", Diagnostic Microbiology and Infectious Disease, 79 (2014) pp. 160-165.
Mezger, MSc, Anja et al., "Rapid Antibiotic Susceptibility Testing for Urinary Tract Infections", Uppsala Universitet, Science for Life Laboratory, 1 page, at least as early as Jun. 13, 2014.
Mitteregger et al., "Neutralization of Antimicrobial Substances in New BacT/Alert FA and FN Plus Blood Culture Bottles". Journal of Clinical Microbiology; 2013; 51: 1534-1540. (Year: 2013).
Mothershed, Elizabeth A. et al., "Nucleic Acid-Based Methods for the Detection of Bacterial Pathogens: Present and Future Considerations for the Clinical Laboratory", Clinica Chimica Acta, 363 (2006) pp. 206-220.

(56) References Cited

OTHER PUBLICATIONS

Nilsson, Mats et al., "Padlock Probes: Circularizing Oligonucleotides for Localized DNA Detection", Science, vol. 265 (1994) pp. 2085-2088.
Olson, Walter C. et al., "Shipping Blood to a Central Laboratory in Multicenter Clinical Trials: Effect of Ambient Temperature on Specimen Temperature, and Effects of Temperature on Mononuclear Cell Yield, Viability and Immunologic Function", Journal of Translation Medicine, 2011, 9:26 (https://www.ncbi.nlm.nih.gov/pmc/articles/PMC3063218/pdf/1479-5876-9-26.pdf).
Pezzlo, M. T. et al., "High Recovery of Bacteria and Fungi in Low Concentrations From Liquid Samples", Pocared Diagnostics 2064, 7 pages, at least as early as Jun. 13, 2014.
Prere, M.-F. et al., "Rapid Identification of Bacteria, mecA and Van Genes From Blood Cultures", Pathologie Biologie 55 (2007) pp. 375-377.
Price et al., "Rapid Antibiotic Susceptibility Phenotypic Characterization of Staphylococcus aureus Using Automated Microscopy of Small Numbers of Cells", Journal of Microbiological Methods, 98 (2014) pp. 50-58.
Pulido et al., "Progress on the development of rapid methods for antimicrobial susceptibility testing", J. Antimicrob .Chemother; 2013; 68: 2710-2717. (Year: 2013).
Rajagopal, Soumitra et al., "Eight Gram-Negative Bacteria Are 10 000 Times More Sensitive to Cationic Detergents Than to Anionic Detergents", Can. J. Microbiol. 49 (2003) pp. 775-779.
Ru, Na-dan et al., "Rapid Identification and Susceptibility Testing of Positive Blood Culture Cause by Gram Negative Bacteria", Chinese Journal of Microecology, vol. 24, No. 11 (Nov. 2012), pp. 1024-1026.
Sage, Jr., Burton H. et al., "Rapid Visual Detection of Microorganisms in Blood Culture", Journal of Clinical Microbiology, vol. 20, No. 1 (1984) pp. 5-8.
Sartor, Maureen et al., "Microarray Results Improve Significantly as Hybridization Approaches Equilibrium", BioTechniques, vol. 36, No. 5 (2004) pp. 790-796.
Sato, Kae et al., "Microbead-Based Rolling Circle Amplification in a Microchip for Sensitive DNA Detection", The Royal Society of Chemistry, Lab Chip, vol. 10 (2010) pp. 1262-1266.
Schweitzer, Barry et al., "Multiplexed Protein Profiling on Microarrays by Rolling-Circle Amplification", Nat Biotechnol., 20, 4 (2002) pp. 1-17.
Siemens, "MicroScan Dried Conventional Gram Negative Panels", Siemens Healthcare Diagnostics (2012) 4 pages.
Smith, James H. et al., "Detection of Nucleic Acid Targets Using Ramified Rolling Circle DNA Amplification: A Single Nucleotide Polymorphism Assay Model", PLOS One, vol. 8, Issue 5 (2013) pp. 1-8.
Spezzotti, Gianpiero, "Technical Notes on the Correct Configuration of the Alfred 60/AST Device for the Detection of Urinary Tract Infections", Journal of Clinical Microbiology, vol. 52, No. 5 (2014) pp. 1805-1806.
Sullivan, Nadine M. et al., "Practical Aerobic Membrane Filtration Blood Culture Technique: Development of Procedure", Journal of Clinical Microbiology, vol. 1, No. 1 (1975) pp. 30-36.
Sullivan, Nadine M. et al., "Practical Aerobic Membrane Filtration Blood Culture Technique: Clinical Blood Culture Trial", Journal of Clinical Microbiology, vol. 1, No. 1 (1975) pp. 37-43.
Tenover, Fred C. et al., "Vancomycin-Resistant Staphylococcus aureus Isolate From a Patient in Pennsylvania", Antimicrobial Agents and Chemotherapy, vol. 8, No. 1 (2004) pp. 275-280.
Torio, Celeste M. et al., "National Inpatient Hospital Costs: The Most Expensive Conditions by Payer, 2011", Agency for Healthcare Research and Quality, Rockville, MD, HCUP Statistical Brief #160 (2013) 12 pages.
Unico Catalog, Laboratory/MedicalNeterinary Equipment; 2012: p. 1-39. (Retrieved from internet: Accessorieshttps:// assets.tequipnnent.net/assets/1/7/UNICO-Lab-Equipment-Catalog.pdf, retrieved on Nov. 6, 2020). (Year: 2012).
Van Belkum, Alex, et al., "Next-Generation Antimicrobial Susceptibility Testing", Journal of Clinical Microbiology, vol. 51, No. 7 (2013) pp. 2018-2024.
Wei, Cheng-Wey et al., "Using a Microfluidic Device for 1 µl DNA Microarray Hybridization in 500 s", Nucleic Acids Research, vol. 33, No. 8 (2005) pp. 1-11.
Whittier, S. et al., "Evaluation of the BD Phoenix Automated Microbiology System for Antibiotic Susceptibility Testing of Streptococcus pneumoniae", American Society for Microbiology 106th General Meeting (2006) 4 pages.
Wiles, T. et al., "Rapid Antimicrobial Susceptibility Testing in Phoenix", American Society for Microbiology 99th General Meeting (1999) 3 pages.
Wu, S.-J. et al., "Preparation of Milk Samples for PCR Analysis Using a Rapid Filtration Technique", Journal of Applied Microbiology, 96 (2004) pp. 1342-1346.
Zierdt, Charles H. et al., "Development of a Lysis-Filtration Blood Culture Technique", Journal of Clinical Microbiology, vol. 5, No. 1 (1977) pp. 46-50.
Zierdt, Charles H., "Blood Lysing Solution Nontoxic to Pathogenic Bacteria", Journal of Clinical Microbiology, vol. 15, No. 1 (1982) pp. 172-174.
Zierdt, Charles H. et al., "Lysis-Filtration Blood Culture Versus Conventional Blood Culture in a Bacteremic Rabbit Model", Journal of Clinical Microbiology, vol. 15, No. 1 (1982) pp. 74-77.
Zierdt, Charles H., "Simplified Lysed-Blood Culture Technique", Journal of Clinical Microbiology, vol. 23, No. 3 (1986) pp. 452-455.
International Search Report and Written Opinion of International Application No. PCT/EP2016/058952 dated Aug. 24, 2016, 11 pages.
International Search Report and Written Opinion of International Application No. PCT/EP2017/059542 dated Jul. 17, 2017, 13 pages.
U.K. Search Report of British Application No. GB1507026.1 dated Oct. 27, 2014, 4 pages.
U.K. Search Report of British Application No. GB1606991.6 dated Jan. 26, 2017, 4 pages.
U.K. Search Report of British Application No. GB1617353.6 dated Jan. 31, 2018, 7 pages.

* cited by examiner

MEDICAL SAMPLE TRANSPORTATION CONTAINER

This application is a divisional application of U.S. patent application Ser. No. 15/569,036 which was filed on Oct. 24, 2017 and is still pending. That application in turn was the national phase of International Application Serial No. PCT/EP2016/058952 which was filed on Apr. 21, 2016 and which claims priority to British Patent Application No. 1507026.1 which was filed on Apr. 24, 2015.

The present invention relates to a portable apparatus for transport of a medical sample in a blood culture flask, and a method of handling a medical sample in a blood culture flask.

Medical conditions caused by microbiological agents are generally diagnosed through the testing of a sample taken from a patient. A key objective (particularly with life-threatening conditions with a rapid progression rate, such as sepsis) is to have the sample analysed as quickly as possible, so that the microbe can be identified and an appropriate and targeted treatment administered.

Many microbiology labs run around the clock, and yet still there are unnecessary delays. In particular, there is often a long lead-time from the time that the sample (for example, blood) is taken to the time that the sample is placed in an automated culture cabinet in the microbiology laboratory. Blood samples are collected, transported and cultured in the culture cabinet within blood culture flasks (blood culture flasks). Examples of blood culture flasks are BacT/Alert® (Biomerieux), Bactec™ (Becton Dickinson) and Versa-Trek® (Thermo Fisher).

There is a risk of yielding a false negative if culturing of the sample has occurred before the sample is placed in the automated culture cabinet (i.e. pre-culturing). For this reason, samples are generally transported to the microbiology laboratory in containers (which may be insulated) which are either maintained at room temperature, or are cooled to below room temperature.

Most prior art transport containers for culturing are within the field of cell-culture and tissue transportation as the cost and need are higher in that field. One example of such a container is described in U.S. Pat. No. 8,074,465. This discloses a thermally insulated transport container system comprising: a closable container having a thermally insulated portion, the container being configured for storage or shipment of a skeletal myoblast cell-based product; a sealable canister within the container, the canister being configured for holding the skeletal myoblast cell-based product; and a refrigerant within the container, the refrigerant being configured to maintain an internal temperature in the canister in the range of −5° C. to 15° C. for a period of at least 72 hours.

The prior art also includes containers that are designed for transport and heating of biological material in order to preserve the biological material. For example, GB 2055530 discloses an electrically heated case for transporting infusion solution and U.S. Pat. No. 6,028,293 discloses a temperature controlled container for transporting biological tissue including human skin. It is however important to realise that the purpose of such devices is considerably different to the purpose of the device of U.S. Pat. No. 8,074,465 and the like, since preservation of biological materials is done for very different reasons than incubation of medical samples to culture the sample. Indeed, one skilled in the art would not consider the use of a tissue preservation device as in GB 2055530 or U.S. Pat. No. 6,028,293 for incubation of a sample as proposed in U.S. Pat. No. 8,074,465.

An incubation device using heating in a portable device is described in US 2013/226032. The disclosure relates to stimulation of whole blood and then chilling of the blood in the same container during transport and storage of the blood. The blood is held in blood vacuum collection tubes and manual processing of these tubes is required to manually add active ingredients such as anticoagulants and stimulants, and to then introduce a leukocyte membrane to the tubes.

According to a first aspect of the present invention, there is provided a portable apparatus for transport and incubation of a medical sample in a blood culture flask, the apparatus comprising: a sealable container having a thermally insulated compartment for receiving the blood culture flask; a heater for heating the medical sample to a temperature suitable for pre-culturing of the sample; and an agitator for mechanically agitating the blood culture flask.

The heater may preferably be for maintaining the sample at a temperature suitable for pre-culturing of the sample. Here, maintaining the temperature means holding the temperature of the sample within a given range (at which pre-culturing can still take place) for a predetermined length of time, or until the blood culture flask is removed from the container. Preferably the sample is maintained at a temperature which is within 5 degrees of the optimal temperature, more preferably within 2 degrees of the optimal temperature. In order to maintain the sample at a required temperature after heating the heater should be arranged to provide sufficient heat to replace the heat lost from the thermally insulated compartment during use of the device to transport the sample.

The inventors have made the non-obvious realisation that for some diagnostic systems, such as that described in WO2015/189390, pre-culturing with heating and agitation is not problematic. For example, pre-culturing is acceptable if the analysis is not dependent on a positive determination of microbial growth, i.e. detecting a positive sample in a conventional culture cabinet. Where pre-culturing is acceptable, the container need not be cooled as there is no need to prevent (or reduce the degree of) pre-culturing. Furthermore, the inventors have realised that it is advantageous to pre-culture the sample as it is in transit to the laboratory, because this allows the sample testing to be run faster once it is received at the laboratory performing the testing. Therefore, the inventors have recognised that it is advantageous to heat the sample to above room temperature, whilst agitating the sample periodically or continuously rather than cooling it or maintaining it at room temperature.

The thermally insulated compartment is provided inside the sealable container, that is, it is an interior space/volume within the sealable container. The thermally insulated compartment may comprise a sleeve for holding the blood culture flask. It is advantageous for the sleeve to be removable and preferably disposable. A removable sleeve allows for ease of handling of the sleeve with the blood culture flask within it, as well as the possibility to insert and remove the blood culture flask with the sleeve outside of the apparatus. A disposable sleeve ensures that the risk of contamination from contact with the outside of the blood culture flask can be avoided. A new sleeve can be used for each use of the portable apparatus, with the portable apparatus never coming into direct contact with the blood culture flask. The agitator may agitate the blood culture flask by movement of the sleeve.

The sleeve may be arranged to resiliently deform during insertion and removal of the blood culture flask, and to hold the flask securely due to the resilience of the sleeve whilst the flask is fully inserted. For example the sleeve may comprise resilient tines arranged to clasp a shoulder of the flask when the flask is inserted, and to be pushed resiliently outwardly and pass around a circumference of the main body of the flask when the flask is being inserted or removed.

Agitation during heating ensures even heating of the sample as well as promoting effective culturing of the sample. The use of agitation has been found to be important to the operation of the pre-culturing apparatus. The proposed apparatus can hence provide improved culturing compared to devices without an integrated agitator device. Microbiological agents in the sample can be kept in suspension and the agitation also allows the sample to be aerated. The agitator may roll, tilt, displace, shake, rotate, or repeatedly invert the blood culture flask. Alternatively or additionally, the blood culture flask may include a magnetic stir bar and the agitator may comprise a means for generating a rotating magnetic field (for example, a rotating magnet or a set of stationary electromagnets), the agitator then being operable to cause the magnetic stir bar to spin, thereby stirring the sample. A further alternative is to use thermal convection by differential temperature on the different sides of the BCF.

In this case where the blood culture flask itself moves, with or without a sleeve, the compartment and container must be sized appropriately so as to allow the required degree of movement. The compartment may hence be larger than the blood culture flask in order to allow for movement of the blood culture flask within the compartment. The blood culture flask may be received within a sleeve within the compartment, and the sleeve may be moved by the agitator (relative to the stationary compartment) so as to control movement of the blood culture flask. The container may then receive the compartment snugly. Alternatively, the compartment may be sized so as to receive the blood culture flask snugly, and the container may be sized so as to allow movement of the compartment itself within the container.

The blood culture flask may be rotated and/or rocked about one or more axis whilst it is a generally horizontal position, a generally vertical position, or any other orientation. In this context horizontal and vertical references the orientation of the main axis of the flask, i.e. the axis of rotation for a bottle shaped flask. Typically the opening of the flask will be at the top of this axis when the flask is held vertically.

One possible arrangement for an agitator is to place the blood culture flask in a horizontal position within the container, and for the agitator to be arranged to roll the blood culture flask about its axis and/or to rock the axis in a see-saw motion in order to agitate the blood culture. It is preferred in this case for the portable apparatus to be arranged to be transported horizontally, and therefore the apparatus may be provided with markings or instructions indicating an orientation with the flask horizontal during transport.

Another possibility is to provide an off-centre (i.e. off-axial) rotational movement of one or both of the ends of the blood culture flask, e.g. the top of the blood culture flask, the bottom of blood culture flask or both the top and the bottom of the blood culture flask. This could be done with the blood culture flask generally horizontal or generally vertical, for example by combining a horizontal rolling, off-axis, rotation producing a back and forth sloshing movement of the sample fluid, or combining a vertical spinning and off-axis rotation producing a vortex and a swirling motion within the fluid. Angles between the horizontal and the vertical can also be used, for example a 45° angle of the axis of the flask. Off-axial rotating movement may be provided by an eccentric cam or a yoke/gimbal device, for example. The axis of symmetry of the blood culture flask can be misaligned with the axis of rotation of the cam, and the two axes are non-parallel, such that the blood culture flask rotates in an off-axial manner.

The blood culture flask may be rotated continuously or intermittently, and optionally with changes in the direction of rotation. In this way the degree of agitation that is applied via the rotation can be controlled.

One example embodiment uses a swash plate type formation, with the blood culture flask coupled to a rotation device with an axis of symmetry of the blood culture flask out of alignment with the axis of rotation of the rotation device. One way to achieve this is to mount the blood culture flask with the base of the flask being non-perpendicular to the axis of rotation, for example by having a slanted surface, a spacer structure, a wedge or any other structure ensuring that the base of the flask does not sit perpendicular to the axis of rotation of the rotation device. The mounting of the blood culture flask may be via a sleeve that holds the flask as explained above.

Another example uses a yoke with the blood culture flask hung vertically from a pivoted connection and the centre of mass of the flask below the pivot point. This yoke can be mounted for rotation and when the yoke is spun the hanging flask will swing outward allowing for a swirling motion to be applied to the sample in the flask.

The rotation device may include a wheel rotated by a motor, with the radial direction of the wheel being perpendicular to the axis of rotation, which may pass through the centre of the wheel. An off-centre axis could provide a further option for an agitation action. The apparatus may be arranged so that the blood culture flask is held on the wheel for rotation with the wheel, for example by means of a suitable key or other interconnection, including a yoke as described above, and so that the blood culture flask has its base non-parallel with the radial direction of the wheel during rotation. The off-centre movement can be combined with a rolling movement while consuming only low energy for the agitation.

Another possibility is to allow a horizontal rolling movement of the blood culture flask, while horizontally positioned, to create agitation within the sample.

The agitator may be controlled by a controller. The agitation may be recorded by an accelerometer to measure the degree of agitation of the blood culture flask during transportation. In this case the controller may adjust the duration and/or the degree of agitation to provide a pre-set minimum agitation of the sample. The degree of agitation recorded by the accelerometer may be shown on the display on which the recorded by the timer is displayed, or on a separate display.

The agitation device may agitate the sample constantly, or may agitate the sample intermittently, i.e. by cycling through a period of agitating constantly, followed by a period of no agitation. The lengths of the agitation period and non-agitation period can be chosen as appropriate and may be controlled by the controller.

The agitator may be mainly or entirely within the thermally insulated compartment. If the agitator, or at least the moving parts of the agitator, is within the thermally insulated compartment then the risk of loss of heat through openings within the thermally insulated compartment is minimised. Moreover, in the case where an electrical motor is used for agitation then the electrical motor can advantageously be within the insulated compartment since heat loss from the motor will then contribute toward heating of the thermally insulated compartment.

As noted above, the apparatus is suitable for transport of a medical sample in a blood culture flask, and is therefore sized appropriately. Further, the apparatus may include a blood culture flask such as a flask as described below. It is to be noted that a blood culture flask is a recognised form of flask in the field of the invention and denotes a flask that is specifically designed for and provided for culturing of medical samples such as blood samples. It would not, for example, be obvious to use such a flask in a device intended for purposes other than culturing of medical samples, and thus even if a prior art device for preserving biological matter (such as the devices in GB 2055530 or U.S. Pat. No. 6,028,293) was capable of holding a blood culture flask it would nonetheless not be obvious to insert a blood culture flask into such a device. Instead one skilled in the art would only look to blood culture devices when considering how to handle blood culture flasks. Moreover, it is not considered to be obvious to adapt specialised medical devices for other vessels, such as the vacuum collection tubes of US 2013/226032, to use a blood culture flask.

The apparatus may, for example, be suitable for transportation of a Becton Dickinson Bactec™ blood culture flask and may comprise such a flask. These have a maximum height of 147 mm and a maximum diameter of 39.7 mm. Alternatively, or additionally, the apparatus may be suitable for transportation of a Biomeriux BactAlert® blood culture flask. These have a maximum height of 117 mm and a maximum diameter of 35 mm. A further alternative is the apparatus may be suitable for transportation of a Thermo Fisher VersaTrek® blood culture flask and may comprise such a flask. The 40 ml VersaTrek® flask has a maximum height of 124 mm and a maximum diameter of 40 mm. The 80 ml VersaTrek® flask has a maximum height of 105 mm and a maximum diameter of 57 mm.

Alternatively or additionally, the apparatus may be suitable for transportation of any other blood culture flask, preferably having a volume of less than 200 ml, more preferably less than 100 ml and most preferably less than 50 ml, and having known dimensions, and the apparatus may comprise such a blood culture flask.

In some examples the apparatus includes a blood culture flask and also a medical sample within the blood culture flask. The medical sample is preferably a sample provided in the flask in a state that requires culturing in relation to subsequent processing of the sample. The medical sample may be a blood sample requiring culturing to enable identification of micro-organisms in the blood. The medical sample may be a sample taken from a patient in order to provide information about the patient's medical condition. The sample may be a sample taken from a patient for the purpose of detecting and characterising a microorganism in the sample, for example by using a method as described in WO2015/189390. The sample may be provided in the flask in an initially uncultured state, with culturing of the sample then occurring during transport of the sample in the flask within the apparatus. The apparatus may thus comprise an uncultured medical sample that requires culturing, a partially cultured medical sample, or a sample that has been cultured sufficiently to allow for further processing and/or testing of the sample, for example diagnostic testing such as that described in patent application WO2015/189390.

The apparatus may have outer dimensions allowing it to be transported in a pneumatic tube system.

The thermally insulated compartment is preferably designed with suitable dimensions for receiving the blood culture flask, for example it may include a cylindrical space, which may be arranged to receive a flask with a diameter of 57 mm or below and a height of 147 mm or below. However, in some embodiments the compartment may be larger in order to allow for movement of the flask within the compartment. It is preferred for the thermally insulated compartment to receive all of or at least the majority of the flask.

The thermally insulated compartment may be lined with a resilient material and/or be provided with deformable elements for securely holding the flask. This may include a sleeve as described above. With the use of deformable/resilient elements the interior of the compartment may be smaller than the flask when no flask is present, and then deform to accommodate the flask when the flask is inserted. In order to allow for a range of flasks with different sizes to be accommodated by a single design of apparatus the apparatus may be equipped with an adjustment mechanism for adjusting the size of the compartment to fit flasks for different sizes. The adjustment mechanism may include the resilient material and/or deformable elements mentioned above. The adjustment mechanism may alternatively or additionally include one or more sliding elements (or detachable and movable elements) as parts of the walls of the compartment. For example, on or more of the walls may have a Velcro attachment to the sides of the sealable container, and the point of attachment may be movable by detaching the Velcro and then re-attaching it in a different position.

The container may be configured to hold only one blood culture flask. Alternatively, the apparatus may be configured to hold a plurality of blood culture flasks, for example, two, three, or four blood culture flasks. The apparatus may be configured to receive the plurality of blood culture flasks within a single thermally insulated compartment (i.e. the thermally insulated compartment is sized to accommodate a plurality of blood culture flasks) or may comprise a plurality of thermally insulated compartments, each for receiving a single blood culture flask. Where a plurality of thermally insulated compartments is provided, each compartment may be heated (and/or monitored and controlled, as described below) separately. It may be possible to separate the thermally insulated compartment that holds the blood culture flask from the container. The separable thermally insulated compartment may be a consumable. The separate compartments may be transported individually.

The apparatus may comprise a controller for controlling the heater to maintain a pre-set temperature. This may allow the sample to be maintained at a precise and accurate temperature. The controller for controlling the heater may be the same as the controller for controlling the agitator.

The apparatus may comprise a temperature sensor for monitoring the temperature in the interior of the thermally insulated compartment. Where both a controller and temperature sensor are provided, the controller may be in communication with the temperature sensor so as to receive the measured temperature output from the temperature sensor. The controller may be operable to adjust the heater in accordance with the temperature measured by the temperature sensor, preferably in a feedback control system.

The heater may include a chemical heater. The chemical heater may be a single-use disposable heater, such that a new chemical heater is used each time a blood culture flask is pre-cultured. The chemical heater may for example make use of the heat released by catalysing rusting of iron or dissolving calcium chloride. The heater may for example make use of an exothermic reaction between a plurality of reagents. Alternatively, the heater may make use of exothermic reactions such as phase-change materials e.g. exothermic crystallisation of a supersaturated sodium acetate solution for example. Such heaters may be re-usable (and may be regenerated for re-use by placing in boiling water, for example).

The heater may include an electrical heater such as resistance heater, for example a coil of wire, or a kapton heater, each preferably powered by a battery. The output of the electrical heater may be controlled by the controller, which, as mentioned above, may control the heater responsive to temperature measurements from a temperature sensor. This may allow the temperature to be more precisely controlled. The heater may comprise a combination of different heaters. For example, a chemical heater may be used to raise the temperature of the sample rapidly from room temperature to the desired temperature, and then a resistance heater may be used to more precisely control the temperature once the sample is close to the optimal temperature, with low energy consumption.

The heater may be flexible and/or formed in a curve such as a partial or full tube shape, so that it may be wrapped or placed around at least part of the blood culture flask.

The heater may be activated automatically, for example by loading the sample into the container or by closing the container lid. Alternatively, the heater may be manually turned on by the user. The heater may be operable to heat and preferably maintain the sample at a temperature of 25° C. or higher, and more preferably at a temperature of 30° C. or higher.

The heater may be operable to heat and preferably maintain the sample at a temperature of 45° C. or lower, more preferably at a temperature of 40° C. or lower and most preferably at a temperature of 37° C. or lower. The heater may be operable to heat and preferably maintain the sample at a temperature of 25° C. to 40° C., more preferably 30° C. to 37° C., and most preferably 35° C.

The heater may be operable to heat and preferably maintain the sample within the above temperature ranges for a period of up to 12 hours, 6 hours, 4 hours, 3 hours or 1 hour.

There is of course an interaction between the required heater performance, the thermal insulation of the apparatus, and the outside/ambient temperature. The heater may be arranged to provide the above characteristics for ambient temperatures of 15° C. and above, preferably 10° C. and above and more preferably 0° C. and above. Lower temperature operation will typically not be required, but could be designed for if necessary.

In example embodiments the apparatus includes a power source such as a battery. The battery may be used to power an electrical heater as discussed above, as well as supplying power to a controller of the apparatus. The battery may be accessible via a removable lid or panel in order to allow replacement of the battery. In preferred embodiments the battery is rechargeable, thereby enabling repeated usage of the device without the need to replace the battery. The portable apparatus may be arranged to receive power for recharging the battery from a charging point and the invention extends to a combination of one or more portable apparatus as discussed herein with a charging point for recharging the battery of the portable apparatus. The portable apparatus may receive power via a wired connection, such as a plug and socket arrangement, preferably with the socket on the portable apparatus and the plug on a lead connected to the charging point. Alternatively or additionally the charging point may be arranged for wireless power transmission to the portable apparatus, for example via inductive power transfer. The charging point may be arranged for connection to mains electricity.

The portable apparatus may be arranged to be operable to heat and/or agitate the blood culture flask whilst being charged. In this way the charging point could be used for storage of the portable apparatus whilst it is waiting for the sample to be processed further, and the heating and/or agitation of the sample can be done during this storage without risk of depleting the power level of the portable apparatus.

In general a medical institution would use multiple portable apparatuses simultaneously to allow for handling of many samples at once, perhaps tens or even hundreds of samples. The charging point may be arranged to charge multiple portable devices at any one time, for example more than 10 or more than 50 devices. The charging point could hence be provided with multiple inductive charging pads and/or multiple leads allowing for connection to many portable devices.

The thermal insulation of the thermally insulated compartment may be designed to operate within the same temperatures and to provide a degree of insulation suitable to maintain the required temperature with a given heater. The thermal insulation may include a layer of one or more of silica aerogel, expanded polyurethane, expanded polystyrene, urea foam or the like, in a thickness sufficient to give the required thermal capabilities, for example, at least 1 cm, at least 2 cm, or at least 3 cm, at least 4 cm or more, dependent on the selected heater and the required temperature and time period for pre-culturing. Multiple layers of insulation may be included if necessary. The thermal insulation may fully enclose the thermally insulated compartment and hence may be also included in a lid or other removable opening of the thermally insulated compartment.

The apparatus may comprise a timer for recording the amount of time for which the sample has been pre-cultured. The timer may be set automatically by loading the sample into the container, or may be manually set running by the user. Preferably, the timer is set running automatically when the heater is turned on. The timer may also be in communication with the controller, and the controller may set the timer running at the same time as the controller activates the heater. The communication between the timer and controller may be via RFID or any other means.

Where a timer is provided, the apparatus preferably also comprises a display for showing the time recorded by the timer. As a result, when the sample arrives at the laboratory, the length of time for which the sample has been pre-cultured can readily be assessed.

In some cases the next steps for the sample after transport and pre-culturing will depend on whether or not the sample is "positive", i.e. if bacterial growth has occurred at a detectable level. In some examples the portable apparatus includes a sensor for determining if the sample is positive, as well as an indicator for showing if the sample is positive or not. The indicator may be a light or some other form of display, such as an LCD display. Devices for detecting a positive sample are known in the art in relation to non-portable devices, for example as in U.S. Pat. No. 8,709,748 and EP 2828398, and the inventors have realised that a similar automatic detection of a positive sample could advantageously be implemented with the portable incubation apparatus described here. One possibility is to use an optical sensor such as a photodetector to identify changes in the turbidity of the sample. The optical sensor could be mounted within the apparatus outside of the blood culture flask, for example within a sleeve around the flask. This advantageously means that there is no need to access the medical sample directly in order to determine if there is a positive sample. Another possibility is the use of a pH sensor located within the flask. This might be coupled to the apparatus by a wired or wireless connection to communicate power and/or data in order to allow an indicator on the apparatus to display information relating to the pH within the flask. Biomeriux, Inc. offer features relating to identification of positive samples in technology sold under the trade name Colorimetric relating to the BacT/Alert® blood culture flask mentioned above, and similar techniques have been proposed for the Bactec™ blood culture flask from Becton Dickinson.

The portable apparatus may be a part of a system for testing the medical sample after culturing. Hence, in a second aspect the invention provides a medical sample testing system comprising: a portable apparatus as discussed above for transporting and pre-culturing a medical sample; and a medical sample processing system for further testing of the medical sample. The medical sample processing system may be a microorganism detection device for detecting and characterising a microorganism in the medical sample.

Such a microorganism detection device may comprise a test aliquot extraction device for removing a portion of the contents of the blood culture flask for use as a test aliquot; a culturing device for culturing the medical sample in the blood culture vessel after extraction of the test aliquot, and optionally before extraction of the test aliquot; and a DNA testing device for separating DNA from the test aliquot, and performing nucleic acid tests on the DNA to identify the microorganism and to detect the presence or absence of one or more genetic antimicrobial resistance markers in the microorganism.

In one example the DNA testing device may be arranged to perform the nucleic acid tests using:
i. one or more nucleic acid probes or primers for microbial identification, a probe or primer thereof being capable of hybridising specifically to, or a primer thereof being capable of selectively amplifying, a nucleotide sequence which is identificatory of a given microorganism; and
ii. one or more nucleic acid probes or primers for antimicrobial resistance marker detection, a probe or primer thereof being capable of hybridising to, or a primer thereof being capable of selectively amplifying, a nucleotide sequence representing a genetic antimicrobial resistance marker;
and it is detected whether or not the probes or primers have hybridised to the DNA and/or whether or not the primers have taken part in an amplification reaction;
wherein the microorganism detection device is arranged such that: if the given microorganism is identified by the DNA testing device, then the cultured clinical sample produced by the culture vessel by culturing after extraction of the test aliquot is passed to an antimicrobial susceptibility test device for performing antimicrobial susceptibility test on the cultured clinical sample by monitoring microbial growth by assessing growth or markers for growth, and wherein the type and concentration of antimicrobial agents used in the antimicrobial susceptibility test is determined by the identity of the microorganism and antimicrobial resistance markers detected by the DNA testing device; and if the given microorganism is not identified by the DNA testing device, then the microorganism detection device further cultures the clinical sample in the culture vessel to enable further microbial identification and antimicrobial susceptibility tests to be performed after additional culturing in order to identify the microorganism and determine its antimicrobial resistance profile.

The microorganism detection device used in combination with the portable apparatus may hence for example be a microorganism detection device similar to that described in WO2015/189390. The portable apparatus can advantageously be used to transport a medical sample whilst pre-culturing the sample as a part of a broader method for handling the sample of the type described in WO2015/189390. As noted above, the pre-culturing of the sample during transport can be a significant advantage for methods such as that described in WO2015/189390.

According to a third aspect of the present invention, there is provided a method for handling a medical sample in a blood culture flask, wherein the method includes simultaneous transportation and incubation of the medical sample and comprises: placing the blood culture flask in a thermally insulated compartment of a sealable container; heating the medical sample to a temperature suitable for pre-culturing of the sample, wherein the thermally insulated compartment and the heating are used to keep the medical sample at the temperature suitable for pre-culturing during transport of the sample; and mechanically agitating the blood culture flask to thereby agitate the sample during transport and incubation.

The method is preferably carried out using the apparatus of the first aspect, optionally including any of the preferred features of the first aspect or features of the second aspect. Thus, the sample may be as described above, and the heating/agitation may be as described above, for example.

The method may comprise controlling the degree of heating to maintain a pre-set temperature. The method may comprise monitoring the temperature in the compartment, and may comprise controlling the degree of heating to maintain a pre-set temperature based on the monitored temperature.

The method may comprise heating utilising an exothermic chemical reaction, or by using the heat released by phase-change materials, for example exothermic crystallisation of supersaturated solutions. The method may alternatively or additionally include heating electrically. The method may include heating (and preferably maintaining) the sample to a temperature of 25° C. or higher, and more preferably at a temperature of 30° C. or higher. The sample is preferably heated (and preferably maintained) to a temperature of 45° C. or lower, more preferably a temperature of 40° C. or lower and most preferably a temperature of 37° C. or lower. Preferably the method comprises heating (and preferably maintaining) the sample to a temperature of 25° C. to 40° C., more preferably 30° C. to 37° C., and most preferably 35° C. The sample may be heated and maintained within the above temperature ranges for a period of up to 12 hours, 6 hours, 4 hours, 3 hours or 1 hour.

The method may comprise timing the amount of time for which the sample has been pre-cultured. Timing may be started automatically by loading the sample into the container, or may be manually set running by the user. The method may also comprise displaying the time recorded by the timer.

The method includes agitating the sample, for example by shaking, rotating, or repeatedly inverting the sample. The method may include providing an off-axial rotational movement of the blood culture flask, for example using an eccentric cam, such that an axis of symmetry of the blood culture flask is misaligned with the axis of rotation of the cam, and the two axes are non-parallel. The method may include using an agitator as described above.

The sample may be agitated constantly, or intermittently (i.e. by cycling through a period of agitating constantly, followed by a period of no agitation).

The method of handling a medical sample may include testing of the medical sample after pre-culturing during transport. For example, the method may include detecting and characterising a microorganism in the medical sample.

In example embodiments the method includes removing a test aliquot from the blood culture flask, continuing to culture the medical sample in the blood culture flask, separating DNA from the test aliquot, and performing nucleic acid tests on the DNA to identify a microorganism and to detect the presence or absence of one or more genetic antimicrobial resistance markers in the microorganism The nucleic acid tests may be performed using:
i) one or more nucleic acid probes and/or primers for microbial identification, a probe or primer thereof being capable of hybridising specifically to, or a primer thereof being capable of selectively amplifying, a nucleotide sequence which is identificatory of a given microorganism; and
ii) one or more nucleic acid probes and/or primers for antimicrobial resistance marker detection, a probe or primer thereof being capable of hybridising specifically to, or a primer thereof being capable of selectively amplifying, a nucleotide sequence representing a genetic antimicrobial resistance marker.

In a possible method it is detected whether or not the probes and/or primers have hybridised to the DNA and/or the primers have been extended (e.g. an amplification reaction has taken place); and
if a microorganism is identified in the nucleic acid tests then the method includes performing an antimicrobial susceptibility test on a cultured medical sample obtained from the blood culture flask after the continued culturing, wherein microbial growth in the antimicrobial susceptibility test is monitored by assessing growth or markers for growth, and wherein the type and concentration of antimicrobial agents used in the antimicrobial susceptibility test is determined by the identity of the microorganism and antimicrobial resistance markers detected by the nucleic acid tests, and optionally continuing to culture the medical sample in the blood culture flask; or
if no microorganism strain is identified in by the nucleic acid tests then the method includes further culturing the medical sample to enable further microbial identification and antimicrobial susceptibility tests to be performed to identify the microorganism and determine its antimicrobial resistance profile.

Preferred embodiments of the present invention will now be described by reference to the accompanying figures, in which.

Figure 1:
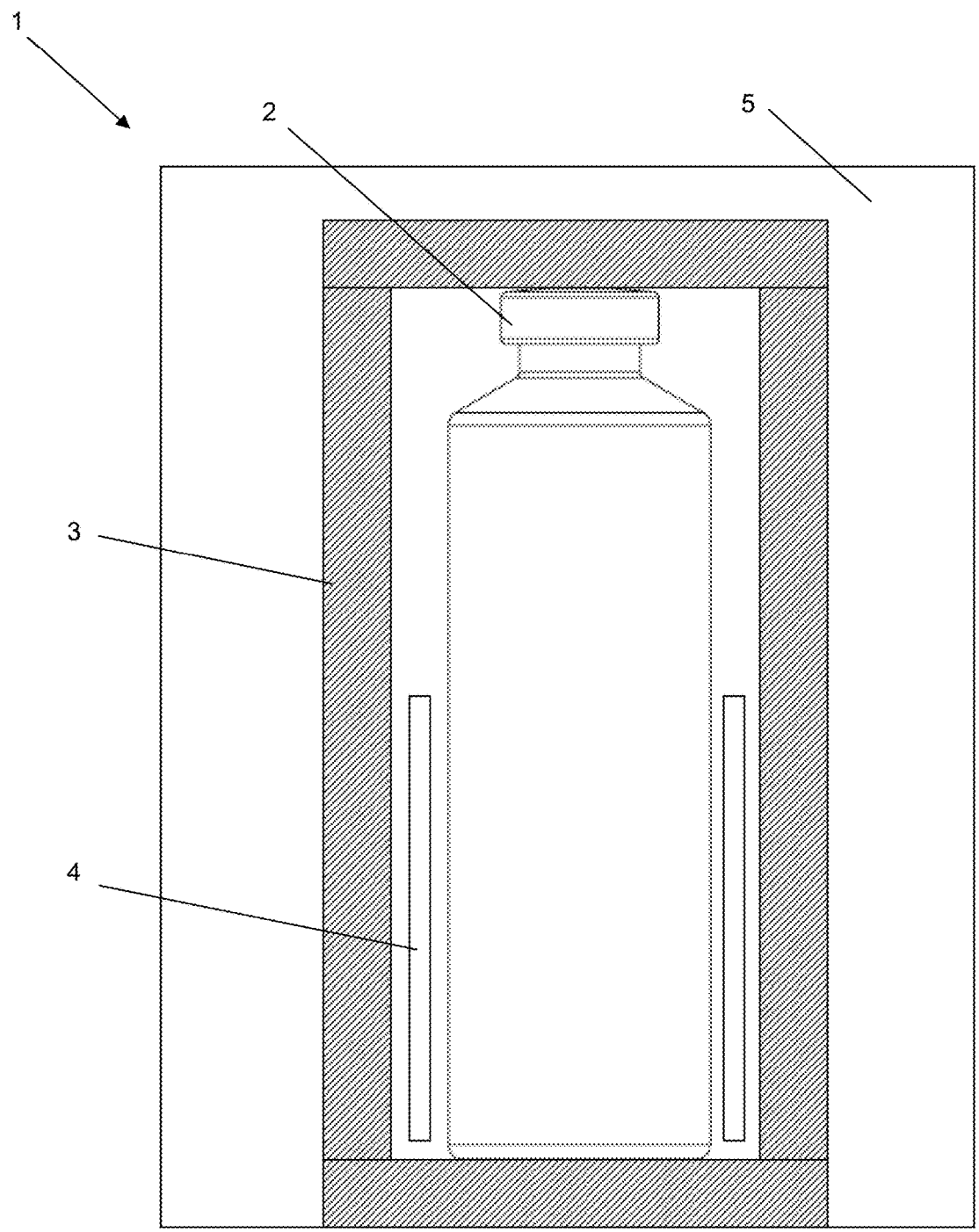
FIG. 1 shows a portable apparatus for transport of a medical sample in a blood culture flask.

The container 1 shown in FIG. 1 is a portable apparatus configured to hold a single blood culture flask 2. The container 1 therefore comprises a single thermally insulated compartment 3 sized to accommodate snugly one blood culture flask. Within the thermally insulated compartment 3 is provided a flexible chemical heater 4 which wraps around the blood culture flask within the thermally insulated compartment 3. The chemical heater is activated manually either shortly before, or shortly after, placing the blood culture flask 2 within the thermally insulated compartment 3. The apparatus is further provided with an agitator, which is not shown in FIG. 1. The agitator might have a similar arrangement to that described below in relation to FIG. 4, for example. The agitator could be within the container 1 to move the flask 2 within the container 1. Or it could be fitted outside the container 1 to move the whole container and thereby also move the flask 2 with the container 1.

Figure 4:
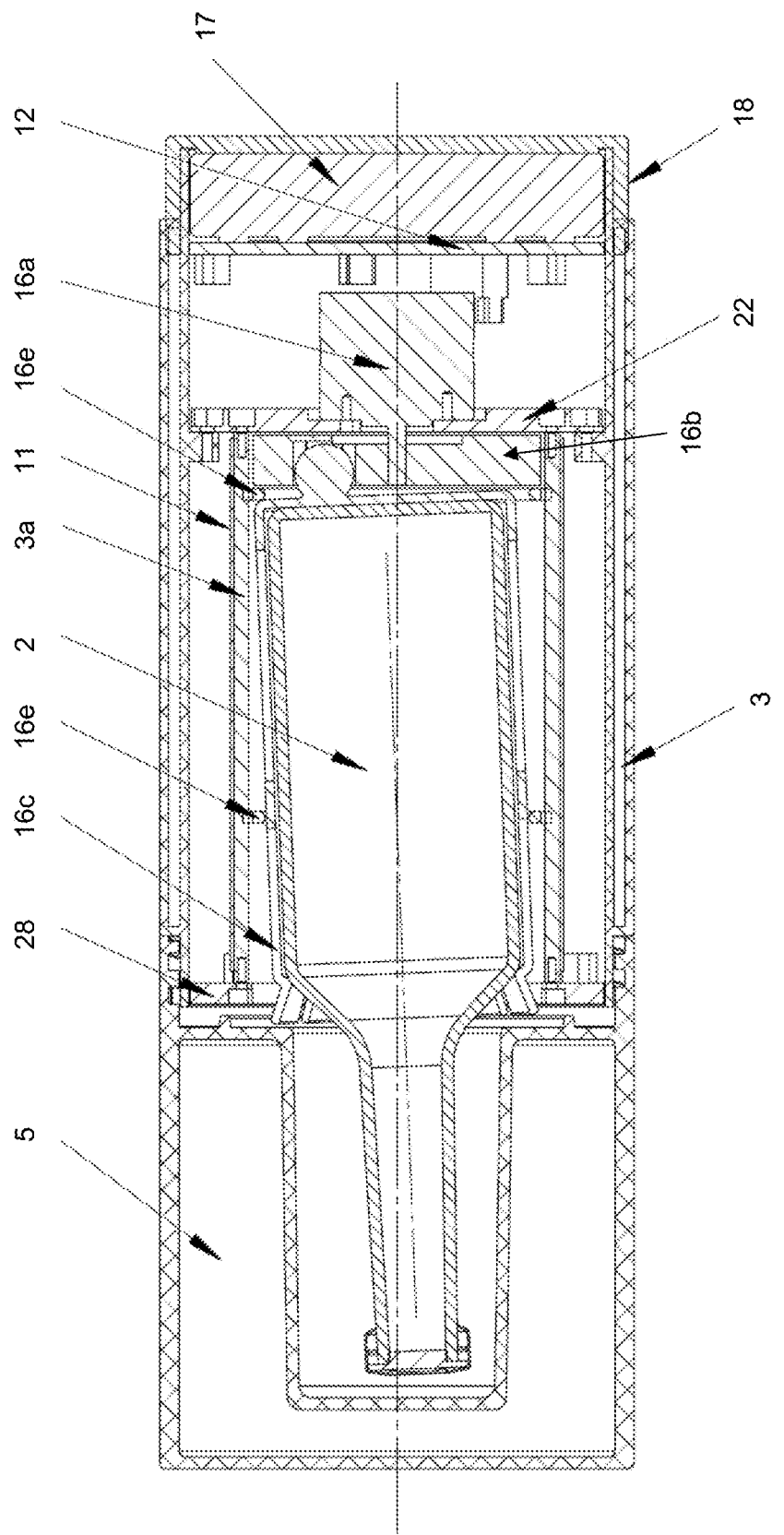
FIG. 4 shows a cross-section of another portable apparatus showing the details of a possible agitation mechanism.

The container 1 is sealed with a lid 5 which may comprise a sealing O-ring 19 (as shown in FIG. 4).

The exterior of the container may include a label (not shown) on which can be written the time at which the sample began pre-culturing (i.e. the time at which the heater was activated).

The container shown in FIG. 1 has a simple construction, which has the advantage that the container is robust and cheap to manufacture. On the other hand, it may be difficult to accurately maintain the blood culture flask at a fixed temperature for a long period of time using this arrangement.

Figure 2:
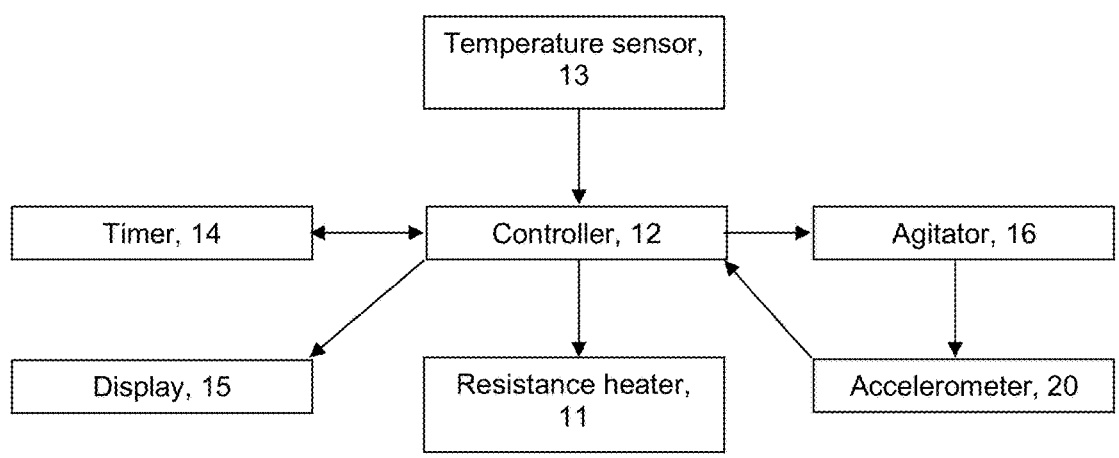
FIG. 2 shows a schematic of a controller, temperature sensor, heater, agitator, accelerometer, timer and display for use in a portable apparatus as shown in the Figures.
Figure 3A:
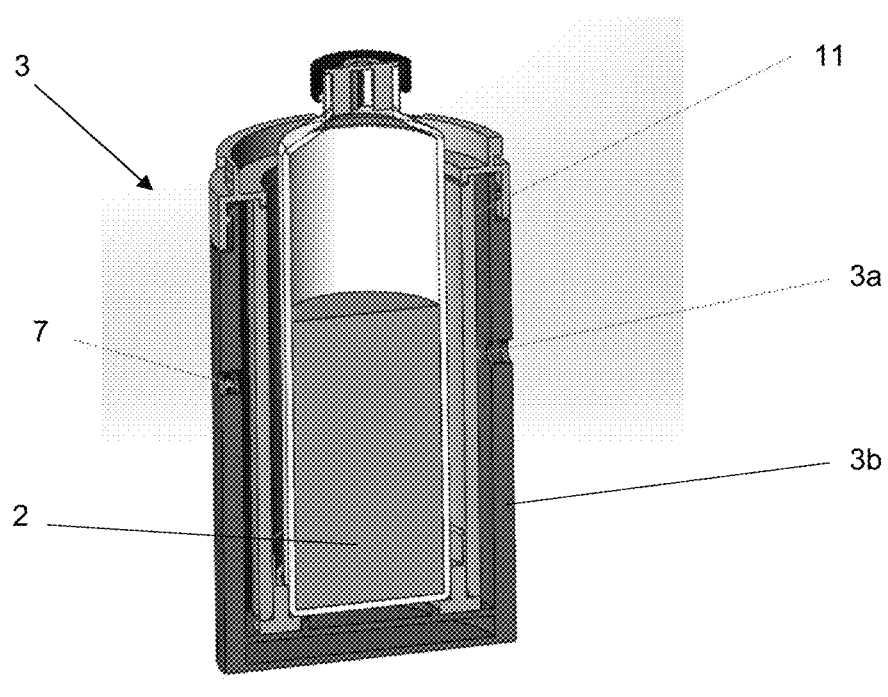
FIGS. 3a and 3b show further details of a part of another a portable apparatus for transport of a medical sample in a blood culture flask.

To address this, instead of the chemical heater of FIG. 1, a controllable electrical heater such as a resistance heater 11 (as shown in FIG. 2) may be used. Such a heater 11 may be used in the container 1 of FIG. 1 with appropriate modifications to the container 1. It may also be used in a container 1 as shown in FIGS. 3a-4, as discussed in more detail below. The resistance heater 11 is in communication with a controller 12, which controls the output of the heater responsive to information from a temperature sensor 13 which measures the temperature within the thermally insulated compartment 3.

The controller may also set running a timer 14 when the heater is activated. The time recorded on the timer may be displayed on an LCD display 15 mounted on an external surface of the container 1. The controller is also operable to control an agitator 16. The agitator 16 shakes the blood culture flask continuously or intermittently in order to aerate the sample. The agitator 16 device is controlled by the controller. The agitation may be recorded by an accelerometer 20 to measure the degree of agitation during transportation. The degree of agitation recorded by the accelerometer timer is displayed on the LCD display 15. Each of the resistance heater 11, controller 12, temperature sensor 13, timer 14, LCD display 15, agitator 16 and accelerometer 20 may be powered by a power supply unit (PSU) 17 (not shown on FIG. 2, but shown on FIG. 4). The PSU may for example be a battery pack, which may be rechargeable, and/or readily replaceable.

Figure 3B:
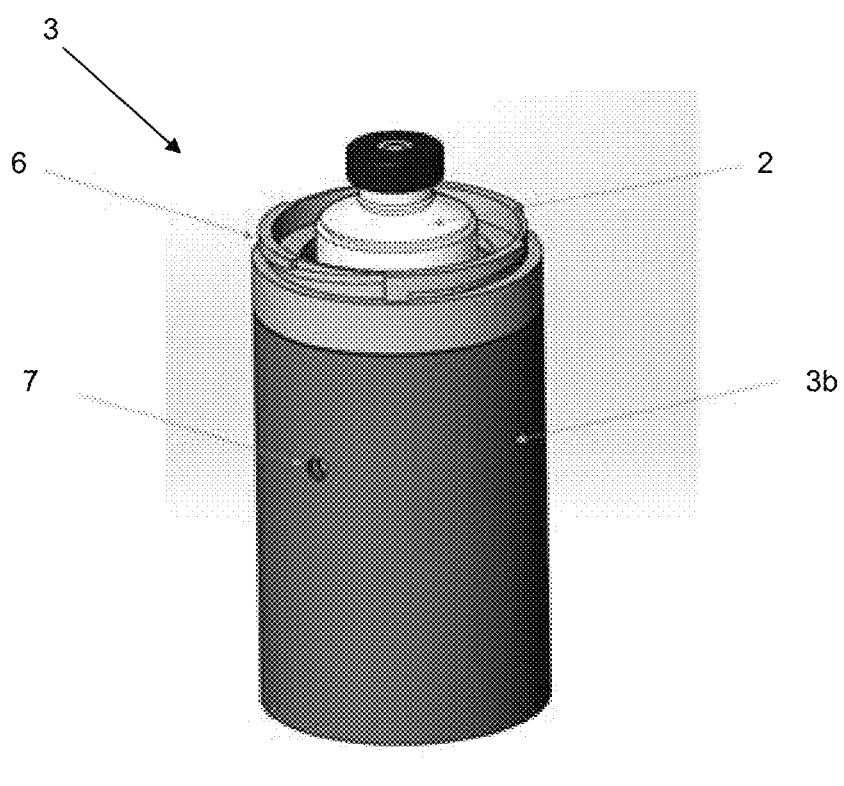

FIGS. 3a and 3b show details of the base of a portable apparatus including the lower part of a thermally insulated compartment 3. As shown in FIG. 3a, the compartment may have a double-walled structure comprising an inner aluminium shell 3a, to which is bonded a kapton resistance heater 11, and an outer plastic shell 3b. The compartment 3 may be sealed with a lid (not shown) attached to the main body of the compartment with a twist-lock connection 6. The lid might be similar to that shown in FIG. 4. The outer plastic shell 3b may comprise two diametrically opposed holes 7 that receive corresponding pins provided in the container (not shown). The pins and holes 7 perform the dual function of providing an electrical connection through to the kapton resistance heater 11, and also provide a pivotal axis about which the compartment 3 can be rotated in order to agitate the sample in the blood culture flask 2. In this way the thermally insulated compartment 3 can be moved using mechanical means to hence mechanically agitate the contents of the blood culture flask 2 within the compartment 3: Alternatively the apparatus of FIGS. 3a and 3b could be adapted so as to include an internal agitator 16 as described with reference to FIG. 4.

FIG. 4 shows a cross-section of another example of a container 1 showing the details of a possible agitation mechanism. Again, the container is a portable apparatus with a thermally insulated compartment 3 for holding a blood culture flask 2. The container 1 of FIG. 4 include a resistance heater 11 similar to that shown in FIG. 3a. The heater 11 together with the agitator 16 can be controlled as described above with reference to FIG. 2. The thermally insulated compartment 3 is closed via top lid 5, which is provided with thermal insulation and has a cavity within the lid 5 sized to enclose the neck of the blood culture flask and allow space for the neck to move as the blood culture flask undergoes agitation via the agitator 16. The top lid 5 is mounted on the main body of the thermally insulated container 3 via a screw fitting as shown. The main body of the thermally insulated container 3 has an inner heated shell 3a and an outer insulating shell similar to that described above. An annular cap 28 seals the main body of the thermally insulated container 3 and bridges between the inner and outer shells. The annular cap 28 has a central opening that receives the sleeve 16c and the blood culture flask 2.

The agitator 16 comprises a motor 16a, a rotating wheel 16b, a sleeve 16c which receives the blood culture flask 2, a off-centre coupling engagement 16d between the sleeve 16c and the rotating cam wheel 16b, and two lock rings 16e which attach the sleeve 16c to the compartment 3 approximately half way along the length of the blood culture flask 2 and at the base of the blood culture flask 2. The motor 16a is separated from the sleeve 16c and the rotating wheel 16b by a motor plate 22, which also provides a mounting point for supporting the motor 16a.

As the motor 16a rotates, the rotating wheel 16b is also driven to rotate, and correspondingly rotates the blood culture flask 2 via the connection of the coupling engagement 16d to the sleeve 16c which holds the blood culture flask 2. The connection of the sleeve 16c to the rotating wheel 16b is such that the axis of symmetry of the blood culture flask 2 is misaligned with the axis of rotation of the motor 16a and cam wheel 16b, and the two axes are non-parallel, such that the blood culture flask 2 rotates in an off-axial manner, fixed in place at the lock ring 16e. In this example this axial misalignment is achieved by the use of a coupling arrangement 16d having a key that cannot be fully fitted within the corresponding recess, such that the key forces the base of the sleeve 16c at one side to be spaced apart from the surface of the rotating wheel 16b, whilst the base of the flask can be closer to or indeed touching the rotating wheel 16b on the other side. This means that the base of the sleeve 16c, and hence the base of the flask 2, is not parallel with the radial direction of the wheel 16b and therefore the axis of rotational symmetry of the flask 2 is not parallel with the axis of rotation of the wheel 16b.

The agitator 16 thus agitates the blood culture flask 2 by movement of the sleeve 16c when the motor 16c rotates the wheel 16b. The sleeve 16c fits closely to the blood culture flask 2, which is a flask 2 of standardised size and hence known dimensions. The sleeve 16c has flexible tine portions at its open end that are arranged to resiliently deform during insertion and removal of the blood culture flask 2. As shown in FIG. 4 these tines hold the flask 2 securely by gripping the shoulder of the flask 2 once it is fully inserted in the sleeve 16c.

The motor 16a is powered by a battery pack 17, which is accessed (for replacement or wired re-charging) via a bottom lid 18. The agitator 16 is controlled by a controller 12, which in this example is a PCB. The motor 16a is advantageously contained within the thermally insulated volume of the thermally insulated compartment 3 such that waste heat from the motor 16a can contribute to heating of the medical sample in the blood culture flask 2.

The thermally insulated compartment 3 comprises thermally insulating material (not shown in all Figures) about the container and with a thickness sufficient to allow the heater to maintain the required temperature. The nature of the thermal insulation can be varied, provided that it provides the necessary reduction in heat loss. Silica aerogel, expanded polyurethane, expanded polystyrene or urea foam may be used, for example.

Optionally the portable apparatus can include a sensor for determining if the sample is positive, as well as an indicator for showing if the sample is positive or not. The indicator may be a light or some other form of display, such as an LCD display. One possibility is to use an optical sensor such as a photodetector (as used, for example, in in EP 2828398) to identify changes in the turbidity of the sample. The optical sensor can be mounted within the sleeve around the flask in the example of FIG. 4 in order to ensure an accurate and repeatable reading of the turbidity of the sample even as the sample is agitated. Another possibility is the use of a pH sensor located within the flask. This might be coupled to the controller by a wired or wireless connection to communicate power and/or data in order to allow an indicator on the apparatus to display information relating to the pH within the flask.

The battery pack 17 can arranged to receive power for recharging the battery from a charging point via a wired connection or via wireless power transmission such as inductive power transfer. The portable apparatus can be provided with a charging point (not shown) that connects to mains electricity and is arranged to charge multiple portable apparatuses simultaneously, for example more than 10 or more than 50 devices. The charging point could hence be provided with multiple inductive charging pads and/or multiple leads allowing for connection to many portable devices. A large hospital could pre-culture up to 250 samples per day, but in batches so a charge station of up to 50 (~100 at most) would suit most needs. Smaller medical institutions could manage with a smaller charging capability, for example 5-10 or 10-50 devices at once.

Figure 5:
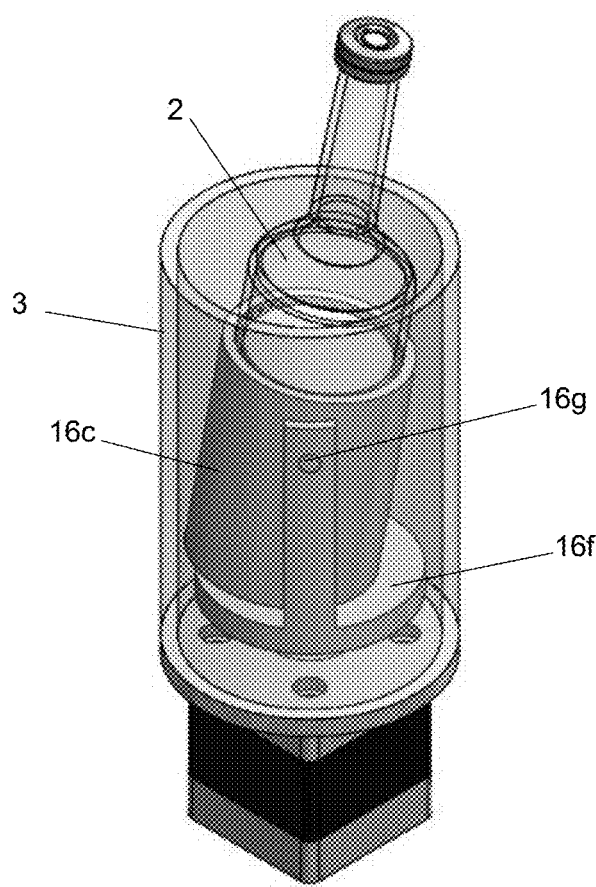
FIG. 5 illustrates an alternative arrangement for the agitation mechanism.

FIG. 5 shows an alternative arrangement for the agitator 16. The blood culture flask 2, thermally insulated compartment 3 and other aspects of the device can be as described above. The thermally insulated compartment 3 is shown transparent in FIG. 5 so that the agitator can be more clearly seen, and other parts (such as the lid and so on) are omitted for the sake of clarity. In this example the agitator 16 has a sleeve 16c similar to that of FIG. 4, but rather than being mounted with an offset axis via a cam wheel 16b as in FIG. 4 the sleeve 16c is held by a yoke 16f. The yoke 16f can be coupled to a motor 16a for rotating the yoke 16f as with the example of FIG. 4, potentially with similar further features such as a controller 12 and a battery pack 17 for powering the motor 16a. Hence, the motor 16a can be mounted beneath the yoke 16f for rotating it around an axis that, during rotation, will be misaligned with the axis of rotational symmetry of the blood culture flask 2. However, unlike the arrangement of FIG. 4, which is designed to work with the sleeve 16c and the blood culture flask 2 held at a fixed offset from the horizontal, the yoke 16f is designed to hold the sleeve 16c and the blood culture flask 2 close to a vertical orientation and to allow a swinging motion during rotation.

The sleeve 16c of this example is held by a pair of pivots 16g on the yoke 16f at a point above the centre of mass of the sleeve 16c and the blood culture flask 2. FIG. 5 shows one of the pivots 16g and the other is at the opposite side of the sleeve 16c in order that the sleeve 16c hangs in a cradle on the yoke 16f. When the portable apparatus is held in the orientation shown in FIG. 5 and there is no movement then the sleeve 16c will hang vertically from the pivots 16g. When the yoke 16f is rotated then since the centre of mass of the sleeve 16c and blood culture flask 2 is below the pivots 16g then the sleeve 16c will tilt as shown in FIG. 5 and the contents of the blood culture flask 2 will be exposed to a vortex/swirling motion to agitate the sample. The motor 16c can be controlled to start, stop, and reverse the rotation to thereby control the degree of agitation. The maximum permitted swing/angle of deflection for the sleeve 16c is restricted by contact of the sleeve 16c with the floor plate of the yoke 16f, and so the geometry of the device sets the maximum offset angle of the axis of the blood culture flask 2 compared to the axis of rotation of the yoke 16f.

A portable apparatus as described in relation to any of the examples above can be used for transportation of a medical sample whilst pre-culturing the medical sample. Thus, the apparatus is used for samples requiring pre-culturing and in particular for samples that have been provided for testing using methods that are not harmed by pre-culturing. For certain testing methods, for example the method as described in WO2015/189390, pre-culturing is an advantage and the use of a portable apparatus for simultaneous pre-culturing and transport of the medical sample for such methods will provide significant advantages in relation to the speed of processing of the samples and the total time required before the results of the testing process are available. Thus, the portable apparatus may be provided as a part of a broader testing system for testing a medical sample. An embodiment hence provides a medical sample testing system comprising: the portable apparatus as described, for example, with reference to any of FIGS. 1 to 5, along with a medical sample processing system for further testing of the medical sample. The portable apparatus is used for transporting and pre-culturing the medical sample, which provides significant benefits in relation to the time taken to obtain a final test result as explained in more detail below.

The medical sample processing system may be a microorganism detection device for detecting and characterising a microorganism in the medical sample similar to that described in WO2015/189390, and hence in one example the portable apparatus is used together with a device comprising a test aliquot extraction device for removing a portion of the contents of the blood culture flask for use as a test aliquot; a culturing device for culturing the medical sample in the blood culture vessel after extraction of the test aliquot, and optionally before extraction of the test aliquot; and a DNA testing device for separating DNA from the test aliquot, and performing nucleic acid tests on the DNA to identify the microorganism and to detect the presence or absence of one or more genetic antimicrobial resistance markers in the microorganism.

The DNA testing device is arranged to perform the nucleic acid tests using:
i. one or more nucleic acid probes or primers for microbial identification, the probe or primer being capable of hybridising specifically to, or a the primer being capable of selectively amplifying, a nucleotide sequence which is identificatory of a given microorganism; and
ii. one or more nucleic acid probes or primers for antimicrobial resistance marker detection, a probe or primer thereof being capable of hybridising to, or a primer thereof being capable of selectively amplifying, a nucleotide sequence representing a genetic antimicrobial resistance marker;
and it is detected whether or not the probe(s) or primer(s_ have hybridised to the DNA and/or whether or not the primer(s) have taken part in an amplification reaction;
wherein the microorganism detection device is arranged such that: if the given microorganism is identified by the DNA testing device, then the cultured clinical sample produced by the culture vessel by culturing after extraction of the test aliquot is passed to an antimicrobial susceptibility test device for performing antimicrobial susceptibility test on the cultured clinical sample by monitoring microbial growth by assessing growth or markers for growth, and wherein the type and concentration of antimicrobial agents used in the antimicrobial susceptibility test is determined by the identity of the microorganism and antimicrobial resistance markers detected by the DNA testing device; and if the given microorganism is not identified by the DNA testing device, then the microorganism detection device further cultures the clinical sample in the culture vessel to enable further microbial identification and antimicrobial susceptibility tests to be performed after additional culturing in order to identify the microorganism and determine its antimicrobial resistance profile.

An example of a method for handling a medical sample in a blood culture flask including transporting the medical sample (advantageously using the apparatus described above) as well as testing the medical sample after pre-culturing during transport. The method comprises: placing the blood culture flask in a thermally insulated compartment of a sealable container; heating the medical sample to a temperature suitable for pre-culturing of the sample, wherein the thermally insulated compartment and the heating are used to keep the medical sample at the temperature suitable for pre-culturing during transport of the sample; and mechanically agitating the blood culture flask to thereby agitate the sample during transport.

The subsequent testing of the medical sample, optionally after further culturing, includes removing a test aliquot from the blood culture flask, continuing to culture the medical sample in the blood culture flask, separating DNA from the test aliquot, and performing nucleic acid tests on the DNA to identify a microorganism and to detect the presence or absence of one or more genetic antimicrobial resistance markers in the microorganism The nucleic acid tests are performed using:
i) one or more nucleic acid probes and/or primers for microbial identification, a probe or primer thereof being capable of hybridising specifically to, or a primer thereof being capable of selectively amplifying, a nucleotide sequence which is identificatory of a given microorganism; and ii) one or more nucleic acid probes and/or primers for antimicrobial resistance marker detection, a probe or primer thereof being capable of hybridising specifically to, or a primer thereof being capable of selectively amplifying, a nucleotide sequence representing a genetic antimicrobial resistance marker.

It is detected whether or not the probes and/or primers have hybridised to the DNA and/or the primers have been extended (e.g. an amplification reaction has taken place); and if a microorganism is identified in the nucleic acid tests then the method includes performing an antimicrobial susceptibility test on a cultured medical sample obtained from the blood culture flask after the continued culturing, wherein microbial growth in the antimicrobial susceptibility test is monitored by assessing growth or markers for growth, and wherein the type and concentration of antimicrobial agents used in the antimicrobial susceptibility test is determined by the identity of the microorganism and antimicrobial resistance markers detected by the nucleic acid tests, and optionally continuing to culture the medical sample in the blood culture flask; or if no microorganism strain is identified in by the nucleic acid tests then the method includes further culturing the medical sample to enable further microbial identification and antimicrobial susceptibility tests to be performed to identify the microorganism and determine its antimicrobial resistance profile.

Figure 6:
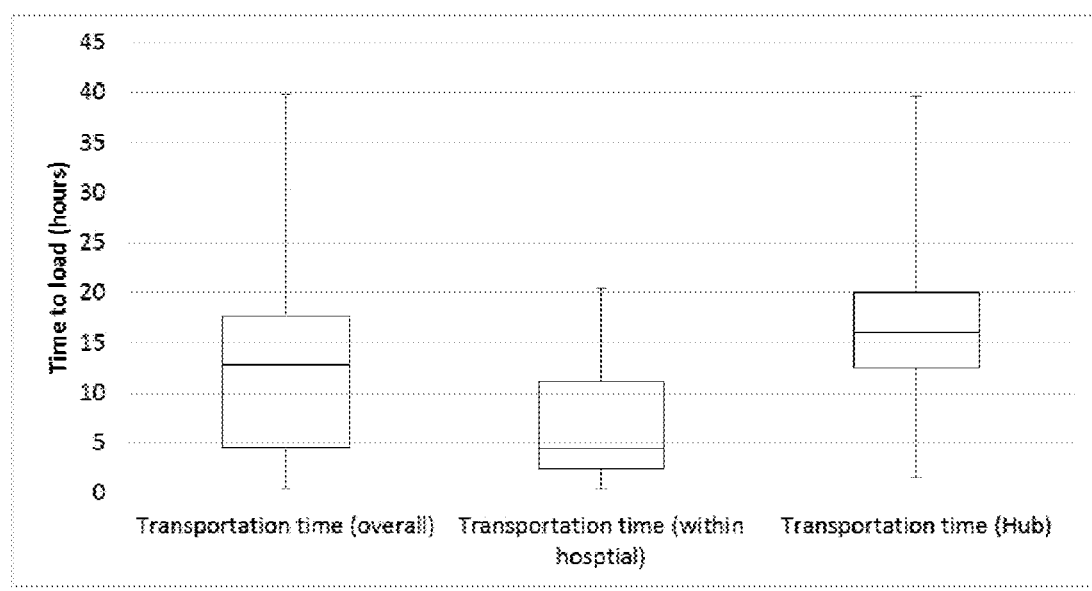
FIG. 6 is a box-whisker diagram showing typical times for transport of samples from a patient to a diagnostic system.

The proposed methods and devices described herein allow for pre-culturing of a medical sample whilst it is in transport. This provides clear advantages in relation to the total time for processing of a sample. FIG. 6 is a box-whisker diagram showing typical times for transport of samples from a patient to a diagnostic system. In prior art systems without pre-culturing, where the sample is essentially inert during transport this time is wasted. Although devices for pre-culturing have been proposed for some purposes, for example as in US 2013/226032, such devices do not provide the agitation required for best performance of the pre-culturing stage.

In medical diagnostics the time to result is often communicated as the time from which a sample is put into a system to time lab result is obtained. For the patient the key issue is of course time to answer from when the clinical sample is taken from the patient to when a lab result is obtained, communicated to treating MD and action taken. The proposed methods and devices provide a way to reduce "time-to-action" for a microbiology in vitro diagnostic system, measured from the time that clinical sample taken until the time that action can be taken to treat the patient.

As an example, for patients with suspected sepsis then blood cultures should always be taken. In the prior art these are transported to the microbiology lab, either at the hospital that the patient is admitted to or to the closest laboratory with microbiology facilities. The time to corrective treatment is very important and it has been shown that mortality increases 7% per hour if not proper treatment is administered. Identifying the causative organism by blood culture enables more focused antibiotics to be used, reducing complications and the risk of emerging antibiotic resistance. Each hour of delay in antibiotic administration increases the risk of death—delay also leads to longer hospital stays and thus greater cost.

The plots of FIG. 6 show the results of analysis of the time to transport a patient sample to the laboratory. This reveals a surprisingly long transportation time, on average in excess of 12 hours. The ability to provide effective culturing during transportation drastically decreases the time to an actionable result. The box-whisker diagram of 500 samples collected at a medium-large sized hospital in Europe. In the box-whisker diagram 50% of the samples fall within the box, the median is shown in the box and the whiskers show minimum and maximum values within each category.

From this data it is evident that the provision of culturing during transportation is hugely beneficial both for samples transported within a hospital as well as between hospitals (hub) for systems that normally require pre-culturing. Examples of such systems are as described in WO2015/189390 as well as other systems today relying on so called positive blood culture flasks and such as e.g. Nanosphere Verigen, (Nanosphere Inc.), Biofire BCID (Biomerieux), and AST/ID from Accelerate Diagnostics as described in e.g. US20150225762. The proposed methods and devices will also shorten time to so called positivity also in so called blood culture cabinets such as e.g. Biomerieux BacTec, Becton Dickinson BactAlert and Thermo Fisher VersaTrek (and similar) as long as the bacterial growth is detected using an absolute measurement and not delta growth after insertion in the system. On average a 5 hour reduction in the time to answer can be achieved within a hospital and a 16 hour reduction in time to answer is possible if samples are shipped between hospitals for systems relying on positive blood culture flasks.

An important aspect for a solution to contribute to faster time-to-action is to streamline workflow. Therefore deposition of the sampled blood culture flasks from the patient at the site of routine transportation to the microbiology lab is crucial. To ensure pre-culturing the incubator then must be transportable and should be capable of both heating and agitating the medical sample during transport.

Figure 7A:
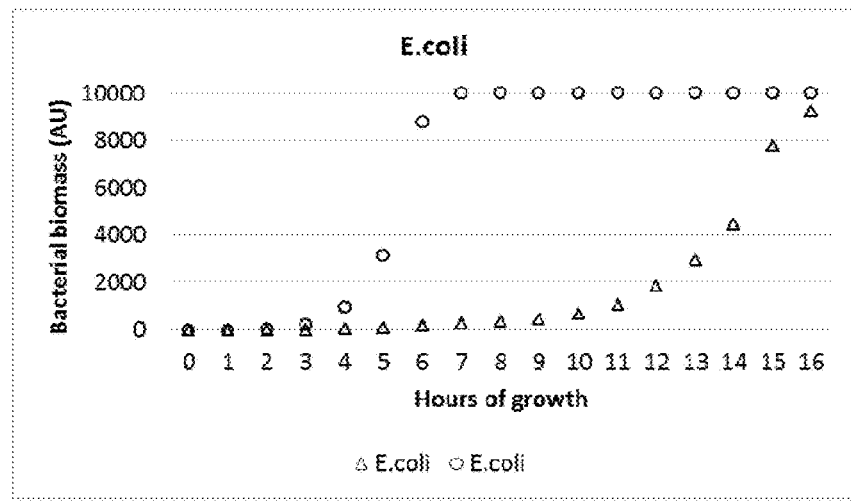
FIGS. 7a-7c show growth of bacteria at room temperature (triangular data points) as compared to at 35° C. (circular data points) for (a) E. coli, (b) S aureus and (c) C. albicans.
Figure 7B:
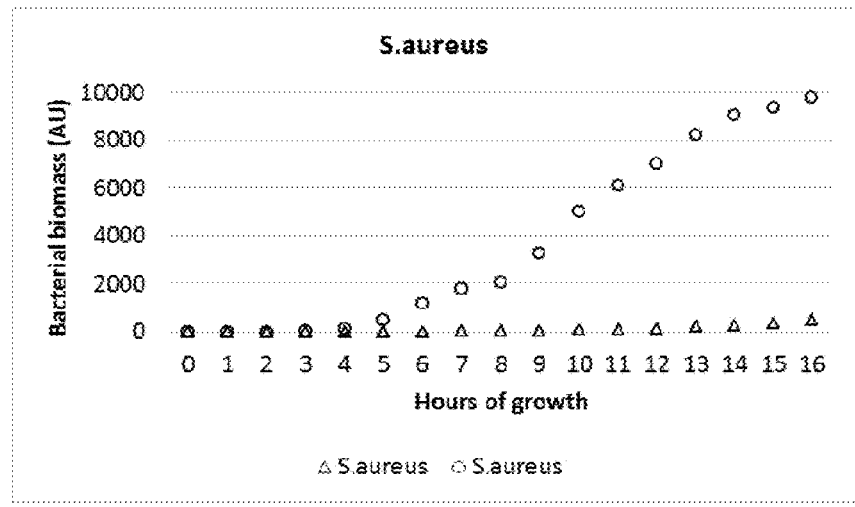
Figure 7C:
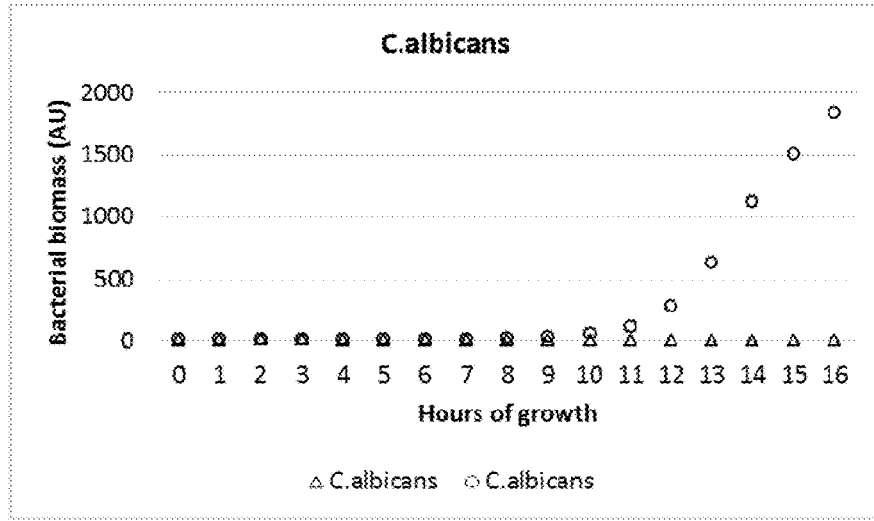

As shown in the examples of FIGS. 7a to 7c it is clear that transportation at room temperature is considerably less effective for stimulation of pathogen growth than transportation at elevated temperature. Three samples with different bacteria were split and allowed to grow in growth media either at room temperature or at 35° C. to simulate transportation at the different conditions. Each hour the amount of bacteria present in the sample were measured using Ocelloscope (Philips, Netherlands) and the Biomass was determined based on images acquired from the Ocelloscope. For the *E. coli* 1E4 CFU/ml were used as a starting sample, for *S. aureus* 2.7E3 CFU/ml and for *C. albicans* 3.6E2 CFU/ml as determined by viable count on non-selective agar plates. *E. coli* is a gram negative, *S. aureus* is a gram positive bacteria and *C. albicans* is a fungi. FIGS. 7a-7c show the growth of bacteria at room temperature (triangular data points) as compared to the growth of bacteria at 35° C. (circular data points) for (a) *E. coli*, (b) *S aureus* and (c) *C. albicans*. There are clear benefits in terms of pre-culturing in the context of diagnostic testing where pre-culturing is needed.

The invention claimed is:

1. A method for handling a medical sample in a blood culture flask, wherein the medical sample is a blood sample, and wherein the method includes simultaneous transportation and incubation of the medical sample in a portable, hand-held apparatus for transport and incubation of the medical sample, the apparatus comprising a sealable container having a thermally insulated compartment for receiving the blood culture flask; a heater; and an agitator, and comprises:
placing the blood culture flask in the thermally insulated compartment of the sealable container;
transporting the medical sample;
pre-culturing the medical sample by, with the heater, heating the medical sample to a temperature suitable for pre-culturing to promote growth of microorganisms, wherein the thermally insulated compartment and the heating are used to keep the medical sample at the temperature suitable for pre-culturing during the transporting of the medical sample; and
with the agitator, agitating the medical sample in the blood culture flask during transportation and pre-culturing of the medical sample.

2. The method as claimed in claim 1, further comprising, after pre-culturing during transport in the thermally insulated compartment, testing of the medical sample for the purpose of detecting and characterizing a microorganism in the medical sample.

3. The method as claimed in claim 1, further comprising timing the amount of time for which the sample has been pre-cultured.

4. The method as claimed in claim 3, wherein the timing is started automatically by loading the sample into the container.

5. The method as claimed in claim 3, wherein the timing is manually started by a user.

6. The method as claimed in claim 3, further comprising displaying the amount of time for which the sample has been pre-cultured.

7. The method as claimed in claim 1, wherein the heating is done by an electrical heater.

8. The method as claimed in claim 1, further comprising controlling the agitator to apply a predetermined degree of agitation.

9. The method as claimed in claim 1, further comprising agitating the sample constantly or intermittently.

10. The method as claimed in claim 1, further comprising controlling the degree of heating to maintain a pre-set temperature.

11. The method as claimed in claim 1, further comprising monitoring the temperature in the compartment and optionally controlling the degree of heating to maintain a pre-set temperature based on the monitored temperature.

12. The method as claimed in claim 1, further comprising monitoring, using an accelerometer, the agitation of the blood culture flask.

13. The method as claimed in claim 1, further comprising determining whether the sample is positive for microbial growth.

14. The method as claimed in claim 1, further comprising maintaining the sample at a temperature of 25° C. to 45° C.

15. The method as claimed in claim 1, further comprising maintaining the sample at a temperature of 30° C. to 37° C.

16. The method as claimed in claim 1, wherein the agitating includes rotating the blood culture flask about a main axis of the blood culture flask.

17. The method as claimed in claim 1, further comprising removing a test aliquot from the blood culture flask, continuing to culture the medical sample in the blood culture flask, separating DNA from the test aliquot, and performing nucleic acid tests on the DNA to identify a microorganism and to detect the presence or absence of one or more genetic antimicrobial resistance markers in the microorganism.

18. The method as claimed in claim 17, wherein the nucleic acid tests are performed using
i) one or more nucleic acid probes and/or primers for microbial identification, a probe or primer thereof being capable of hybridizing specifically to, or a primer thereof being capable of selectively amplifying, a nucleotide sequence which is identificatory of a given microorganism; and
ii) one or more nucleic acid probes and/or primers for antimicrobial resistance marker detection, a probe or primer thereof being capable of hybridizing specifically to, or a primer thereof being capable of selectively amplifying, a nucleotide sequence representing a genetic antimicrobial resistance marker.

19. The method as claimed in claim 17, comprising, detecting whether or not the probes and/or primers have hybridized to the DNA and/or the primers have been extended, and
if a microorganism is identified in the nucleic acid tests, performing an antimicrobial susceptibility test on a cultured medical sample obtained from the blood culture flask after the continued culturing wherein microbial growth in the antimicrobial susceptibility test is monitored by assessing growth or markers for growth, and wherein the type and concentration of antimicrobial agents used in the antimicrobial susceptibility test is determined by the identity of the microorganism and antimicrobial resistance markers detected by the nucleic acid tests, and optionally continuing to culture the medical sample in the blood culture flask; or
if no microorganism strain is identified in by the nucleic acid tests then the method includes further culturing the medical sample to enable further microbial identification and antimicrobial susceptibility tests to be performed to identify the microorganism and determine its antimicrobial resistance profile.

20. The method as claimed in claim 1, wherein the blood culture flask comprises a septum to be perforated for inoculating the flask and subsequently sampling from the flask.

* * * * *